(12) United States Patent
Segreti

(10) Patent No.: US 10,517,848 B2
(45) Date of Patent: Dec. 31, 2019

(54) CANNABIS-BASED BIOACTIVE FORMULATIONS AND METHODS FOR USE THEREOF

(71) Applicant: Louis M. Segreti, San Diego, CA (US)

(72) Inventor: Louis M. Segreti, San Diego, CA (US)

(73) Assignee: Louis M. Segretti, San Diego, CA (US)

( * ) Notice: Subject to any disclaimer, the term of this patent is extended or adjusted under 35 U.S.C. 154(b) by 0 days.

(21) Appl. No.: 16/113,086

(22) Filed: Aug. 27, 2018

(65) Prior Publication Data

US 2019/0046499 A1 Feb. 14, 2019

Related U.S. Application Data

(63) Continuation of application No. PCT/US2017/020531, filed on Mar. 2, 2017.

(60) Provisional application No. 62/303,323, filed on Mar. 3, 2016, provisional application No. 62/326,258, filed on Apr. 22, 2016.

(51) Int. Cl.

| | | |
|---|---|---|
| *A61K 36/00* | (2006.01) | |
| *A61K 31/352* | (2006.01) | |
| *A61K 45/06* | (2006.01) | |
| *A61K 31/05* | (2006.01) | |
| *A61K 31/192* | (2006.01) | |
| *A61K 36/185* | (2006.01) | |
| *A61P 25/20* | (2006.01) | |
| *A61P 25/22* | (2006.01) | |
| *A61P 25/18* | (2006.01) | |

(52) U.S. Cl.
CPC ............ *A61K 31/352* (2013.01); *A61K 31/05* (2013.01); *A61K 31/192* (2013.01); *A61K 36/185* (2013.01); *A61K 45/06* (2013.01); *A61P 25/18* (2018.01); *A61P 25/20* (2018.01); *A61P 25/22* (2018.01)

(58) Field of Classification Search
CPC .................................................... A61K 36/00
USPC ......................................................... 424/725
See application file for complete search history.

(56) References Cited

U.S. PATENT DOCUMENTS

| | | | |
|---|---|---|---|
| 4,279,824 A | 7/1981 | McKinney | |
| 6,730,519 B2 | 5/2004 | Elsohly et al. | |
| 8,895,078 B2 | 11/2014 | Mueller | |
| 2012/0225015 A1* | 9/2012 | Schultz | A61K 51/0404 424/1.65 |
| 2015/0366154 A1 | 12/2015 | Lewis | |
| 2016/0000843 A1 | 1/2016 | Lowe | |

OTHER PUBLICATIONS

"Sensory Perceptual Issues in Austism and Asperger Syndrome, Different Sensory Experiences Different Perceptual Worlds", Bogdashina, O., pp. 77-78.

A.W. Zuardi et al., Action of Cannabidiol on the Anxiety and Other Effects Produced by Delta-9 THC in Normal Subjects.

Allman, M., et al., Developmental neuroscience of time and number: implications for autism and other neurodevelopmental disabilities, Front. Integr. Neurosci (2012) 6:7.

Amresh, S., et al., Cannabis use and cognitive dysfunction, Indian J Psychiatry (2011) Jul.-Sep., 53(3): 187-191.

Antshel, K. M. and Remer, R. (2003) Social skills training in children with attention deficit hyperactivity disorder: a randomized-controlled clinical trial, J. Clin. Child Adolesc. Psychol. 32, 153-16510.1207/15374420360533149.

Barkley, R. A., et al. (1990) Comprehensive evaluation of attention deficit disorder with and without hyperactivity as defined by research criteria, J. Consult. Clin. Psychol. 58, 775-789

Ben-Pazi, H. et al., Abnormal rhythmic motor response in children with attention-deficit-hyperactivity disorder, Developmental Medicine and Child Neurology (2003) 45, 743-45.

Ben-Pazi, H. et al., Age and medication effects on rhythmic responses in ADHD: Possible oscillatory mechanisms, Neuropshychologia (2006); 44, 412-416.

Biederman, J., et al. (1991) Comorbidity of attention deficit hyperactivity disorder with conduct, depressive, anxiety, and other disorders, Am. J. Psychiatry 148, 564-577.

Bruce, B., et al., ADHD and language impairment, Eur Child Adlesc. Psychiatry (2006) 15:52-60

Cantwell, D. P. (1996) Attention deficit disorder: a review of the past 10 years, J. Am. Acad. Child Adolesc. Psychiatry 35, 978-98710. 1097/00004583-199608000-00008.

Cella, M. et al., Commentary: What is the right dose for children? British Journal of Clinical Pharmacology (2010)70:4, 597-603.

Crane, L., et al., Sensory processing in adults with autism spectrum disorders, Autism, May 2009 13:215-228.

Eiraldi, R. B., et al. (2000) Assessing ADHD and comorbid disorders in children: the Child Behavior Checklist and the Devereux Scales of Mental Disorders. J. Clin. Child Psychol. 29,3-16 10.1207/ S15374424jccp2901_2.

Falter, C. and Valdas, N., Interval Timing Deficits and Abnormal Cognitive Development, Front. Integr. Neurosci. (2011) 5:26.

Faraone, S.V., et al., Intellectual performance and school failure in children with attention deficit hyperactivity disorder and in their siblings, J Abnorm Psychol. (1993) 102(4):616-623.

Ghanizadeh, A., Sensory Processing Problems in Children with ADHD, a Systematic Review, Psychiatry Investig. Jun. 2011, 8(2):89-94.

Grant, I., et al., Non-acute (residual) neurocognitive effects of cannabis use: a meta-analytic study, J. Int. Neuropsychol Soc. Jul. 2003, 9(5):679-89.

Han, C.J. and Robinson, J.K., Cannabinoid Modulation of Time Estimation in the Rat, Behavioral Neuroscience (2001) 115(1):243-246.

Hart, C.L., et al., Effects of acute smoked marijuana on complex cognitive performance, Neuropsychopharmacology Nov. 2001, 25(5):757-65.

(Continued)

*Primary Examiner* — Michael V Meller

(57) ABSTRACT

Disclosed are compositions and methods for mitigating a tolerance effect from ingestion of cannabis-based medicines in human subjects, for example, subjects having an increased risk of unresponsiveness to one or more therapeutic agents such as, for example, antidepressants and antianxiety drugs. In some methods, the human subjects have been previously treated with one or more therapeutic agents such as, for example, antidepressants and antianxiety drugs, and have developed at least partial tolerance to the one or more therapeutic agents.

1 Claim, No Drawings

(56) References Cited

OTHER PUBLICATIONS

John, K., et al., The Social Adjustment Inventory for Children and Adolescents (SAICA): testing of a new semistructured interview, J Am Acad Child Adolesc Psychiatry (1987) 26(6):898-911.
Kozcat, D.L., et al., (2002) Eye movement abnormality suggestive of a spatial memory deficit is present in parents of autistic probands, Journal of Autism and Developmental Disorders, 32(6):513 (2002).
Lecavalier, L., et al. (2009) Validation of DSM-IV model of psychiatric syndromes in children with autism spectrum disorders, J. Autism Dev. Disord. 39,278-289.
Leitner, Y., The co-occurrence of autism and attention deficit hyperactivity disorder in children—what do we know? Frontiers in Human Neuroscience (2014) vol. 8, Article 268, pp. 1-8.
Liebeman, H.A., et al., Table of Contents: Pharmaceutical Dosage Forms (vols. 1-3, 1990).
Mallet, P.E. and Beninger, R.J., The cannabinoid CB1 receptor antagonist SR141716A attenuates the memory impairment proeuced by Δ9-tetrahydrocoannabinol or anandamide, Psychopharmacology (Berl) (1998) 140(1):11-19.
Martin, J.S., et al., Brief report, Impaired temporal reproduction performance in adults with autism spectrum disorder, J. Autism Dev. Disord May 2010 40(5);640-6.
Marton, I., et al. (2009) Empathy and social perspective taking in children with attention-deficit/hyperactivity disorder, J. Abnorm. Child Psychol. 37,107-118.
Masi, G., et al., Comorbidity of obsessive-compulsive disorder and attention-deficit/hyperactivity disorder in referred children and adolescents, Comprehensive Psychiatry 2006, vol. 47:1, Jan.-Feb. 2006, pp. 42-47.
Mayes, et al, Research in Autism Spectrum Disorders, Jan.-Mar. 2012, vol. 6(a):277-285, Autism and ADHD: Overlapping and Discriminating Symptoms.
Militerni, R., et al., Repetitive behaviors in autistic disorder, European Child & Adolescent Psychiatry, 11:210-218 (2002).
Mulligan, A., et al. (2009) Autism symptoms in attention-deficit/hyperactivity disorder: a familial trait which correlates with conduct, oppositional defiant, language and motor disorders, J. Autism Dev. Disord. 39, 197-209.
Nava, F., et al., D2 dopamine receptors enable a Δ 9-tetrahydrocannabinol induced memory impairment and reduction of hippocampal extracellular acetylcholine concentration Br J Pharmacol (2000) 130(6):1201-1210.
Noreika V., et al. (2013) Jan. 51(2):235-66, Neuropsychologia, Timing deficits in attention-deficit/hyperactivity disorder (ADHD): evidence from neurocognitive and neuroimaging studies.
Noterdaeme, M., et al., Evaluation of neuromotor deficits in children with autism and children with a specific speech and language disorder, Eur. Child Adolesc. Psychiatry, Oct. 2002; 11(5): 219-25.
Orvaschel H., Psychiatric interviews suitable for use in research with children and adolescents, Psychopharmacol Bull. 1985; 21(4):737-745.
Pardini, D., et al., Chronic Adolescent Marijuana Use as a Risk Factor for Physical and Mental Health Problems in Young Adult Men, Psychology of Addictive Behaviors (2015) vol. 29, No. 3, 552-563.
Pitcher, T, et al., Fine and Gross Motor Ability in Males with ADHD, Developmental Medicine & Child Neurology, Aug. 2003 Volume, Issue 08.
Remington's, The Science and Practice of Pharmacy (2000) Lieberman, H. A. and Lachman, L., Eds., Pharmaceutical Dosage Forms, Marcel Decker, New York, N.Y., 1980.
Reynolds, C.R., Critical measurement issues in learning disabilities, J Spec Educ. (1984) 18(4):451-475.
Rinehart, N.J., Gait function in newly diagnosed children with autism: Cerebellar and basal ganglia related motor disorder; Dev. Med. Child Neurol. Oct. 2006; 48(10); 819-24.
Rommelse, N., et al., Shared heritability of attention-deficit/hyperactivity disorder and autism spectrum disorder, European Child & Adolescent Psychiatry, Mar. 2010, vol. 19:3, pp. 281-295.
Ronald, A., et al. (2010) Exploring the relationship between autistic-like traits and ADHD behaviors in early childhood: findings from a community twin study of 2-year olds, J. Abnorm. Child Psychol. 38, 185-196.
Ronald, A., et al., Evidence and overlapping genetic influences on autistic and ADHD behaviors in a community twin sample, Journal of Child Psychology and Psychiatry, May 2008, vol. 49:5 pp. 535-42.
Rubia et al., Synchronization, anticipation and consistency of motor timing in dimensionally defined children with attention deficit hyperactivity disorder, Perceptual and Motor Skills (1999) 89, 1237-1258.
Rubia, K. et al., Performance of children with attention deficit hyperactivity disorder (ADHD) on a test battery of impulsiveness, Child Neuropsychol. (2007) 13, 276-304.
Rubia, K., et al., Impulsiveness as a timing disturbance: neurocognitive abnormalities in attention-deficit hyperactivity disorder during temporal processes and normalization with methylphenidate, Phil. Trans. R. Soc. B (2009) 364, 1919-1931.
Semrud-Clikeman, M. (2012) The role of inattention on academics, fluid reasoning, and visual-spatial functioning in two subtypes of ADHD, Appl Neuropsychol Child, 1(1):18-29.
Sheppard, B., et al., ADHD prevalence and association with hoarding behaviors in childhood-onset OCD, Depression and Anxiety, vol. 27, Issue 7, pp. 667-674 (2010).
Sofuoglu, M., et al., Cognitive Function as an Emerging Treatment for Marijuana Addiction, Exp. Clin. Psychopharmacol Apr. 2010, 18(2): 109-119.
Solowij, N., Do cognitive impairments recover following cessation of cannabis use? Life Sci. 1995, 56(23-24):2119-26.
Steele, S.D. et al. (2007) Spatial Working Memory Deficits in Autism, Journal of Autism and Developmental Disorders 37 (4): 605-612.
Szelag, E., et al., Temporal processing deficits in high-functioning children with autism, British Journal of Psychology; Aug. 2004, 95:3 pp. 269-282.
Tavassoli, L., et al., Sensory over-responsivity in adults with autism spectrum conditions, Autism, May 2014, vol. 18, No. 4:428-423.
Toplak, M.E., et al., Temporal information processing in ADHD: findings to date and new methods, J. Neurosci. Methods (2006) 151, 15-29.
Tseng, M., et al, Relationship between motor proficiency, attention, impulse and activity in children with ADHD, Developmental Medicine & Child Neurology, Volume, Issue 06, Jun. 2005 pp. 381-388.
Varni, J.W., et al, The PedsQL™: Measurement Model for the Pediatric Quality of Life Inventory, Med Care (1999) 37(2):126-139.
Winsauer, P.J., et al., Cannabiniod ligands and their effects on learning and performance in rhesus monkeys, Behav Pharmacol (1999) 10(5):497-511.
Zimmerberg, B., et al., Imparement of recent memory by marihuana and THC in rhesus monkeys, Nature (1971) 233(5318):343-345.
Kurz, et al , Use of Dronabinol (Delta-9-THC) in Autism: A prospective single-case-study with an early infantile autistic child, Cannabiniods, 5(4):21 (2010).
Strohbeck-Heuhner, et al, Cannabis improves symptoms of ADHD, Cannabinoids, 3(1):1-3 (2008).
PCT Search Report and Written Opinion issued in PCT/US2017/020531 dated May 18, 2017.

* cited by examiner

CANNABIS-BASED BIOACTIVE FORMULATIONS AND METHODS FOR USE THEREOF

RELATED APPLICATIONS

This application is a continuation of International App. No. PCT/US2017/020531 entitled "CANNABIS-BASED BIOACTIVE FORMULATIONS AND METHODS FOR USE THEREOF" filed Mar. 2, 2017 which published in English as WO 2017/151980 on Sep. 8, 2017 which claims priority to U.S. Prov. App. No. 62/303,323, filed on Mar. 3, 2016, and U.S. Prov. App. No. 62/326,258, filed on Apr. 22, 2016, which are each expressly incorporated by reference in its entirety.

FIELD

The present disclosure relates to compositions and methods for mitigating a tolerance effect from ingestion of cannabis-based medicines in human subjects, for example, subjects that have been previously treated with one or more therapeutic agents, such as, e.g., antidepressants and anti-anxiety drugs, and have developed at least partial tolerance to the one or more therapeutic agents.

BACKGROUND

*Cannabis* is a genus of the flowering plant *Cannabis* which has long been used for industrial purposes, medicinal purposes, and as a recreational drug. In fact, cannabis-derived products have long been consumed in various forms for centuries. *Cannabis* is most commonly administered via inhalation or consumption of marijuana-infused food and drink. In particular, the *Cannabis* plant material has been reported to contain various desirable compounds useful in various pharmaceutical dosage forms and methods for medicinal and industrial purposes as well as uses a recreational drug. Cannabinoids, terpenoids, and flavonoids are included amongst the various suitable and desirable compounds. *Cannabis* has been reported to provide substantial benefits to patients suffering from a wide range of symptoms experienced in connection with various medical conditions. For example, *Cannabis* has been reported as being useful to alleviate symptoms associated with anxiety, post-traumatic stress disorder, chronic pain, opiate dependency, paralysis, neuropathy, inflammatory bowel disorders, glaucoma, seizures, epilepsy, autism, cancer, anorexia, spasticity, arthritis, migraine and many other illnesses. As a result, recent research into the use of cannabis-derived products for the treatment of a variety of diseases and conditions has been reaching a feverish pace. In the United States, *Cannabis* has become an important, emerging medical option in a number of states. It is quickly becoming clear that drug formulations containing specific cannabis-derived chemical compounds can have dramatic affect in improving the lives of many patients.

However, it has been reported that a large number of patients treated with therapeutic treatments involving cannabis-derived pharmaceuticals such as, for example, tetrahydrocannabinol (THC) experience significant tolerance effects. These tolerance effects, for instance, can typically be mitigated to some extent by taking a week or two off from consuming the THC-containing pharmaceutical and then re-commencing use. While this is a relatively minor issue for casual users and recreational users, it can present major problems for medicinal users, especially patients struggling with severe, chronic symptoms associated with conditions like ADHD, autism, and other conditions now known to respond favorably to THC, such as Parkinson's disease. Accordingly, given that *Cannabis* and various products derived therefrom have become an important medical option for the treatment of a variety of diseases and conditions, there is a growing need for formulations and methods suitable for effectively mitigating one or more tolerance effects developed from ingestion of cannabis-based products.

It has been reported that tolerance effects may be particularly problematic in chronic, pervasive conditions such as Parkinson's disease, Attention-Deficit/Hyperactivity Disorder (ADHD) and Autism Spectrum Disorder (ASD). Until the publication of the Diagnostic and Statistical Manual of Mental Disorders (DSM-5) in 2013, ADHD and ASD were treated as separately-occurring conditions. The DSM-5 continues to list ADHD and ASD as distinct conditions, but for the first time allows for a co-morbid diagnosis of ADHD with ASD because of the apparent frequency of their co-occurrence. Both disorders are believed to share common genetic influences and are associated with similar cognitive, motor and behavioral deficits that can result in academic, emotional, and adaptive problems in school, at home, and elsewhere.

Medscape (www.medscape.com), a resource widely used by physicians and nurses, states that no pharmacologic agent is considered to be effective in the treatment of the core behavioral manifestations of ASD. Second generation antipsychotics have been approved by the FDA for irritability associated with ASD. Selective serotonin reuptake inhibitors (SSRI) are sometimes prescribed to address the intractable repetitive behaviors seen in some patients suffering from ASD. Also, stimulants are considered an effective treatment for symptoms of hyperactivity. However, the long-term safety and efficacy of these three types of commonly-prescribed drugs has not been established.

According to Medscape, atomoxetine, atypical antidepressants, tricyclic antidepressants, and central acting alpha2 agonists are some of the currently-approved treatments for ADHD. Stimulants, such as methylphenidate, dexmethylphenidate, dextroamphetamine and amphetamine mixtures, dextroamphetamine, lisdexamfetamine, and amphetamine are also considered effective treatments for ADHD, but many stimulants have severe drug interactions and serious adverse side effects.

Thus, there is a need for safer and more effective treatments for ASD and ADHD. An ideal treatment would address many of the cognitive, motor, and behavioral symptoms (or deficits) associated with each condition, along with addressing commonly-occurring comorbid conditions.

In one aspect, the present disclosure relates to methods of using tetrahydrocannabinol (THC) to treat patients diagnosed with ADHD and/or ASD and certain commonly-occurring comorbid conditions.

SUMMARY OF CERTAIN INVENTIVE ASPECTS

This section provides a general summary of the disclosure, and is not comprehensive of its full scope or all of its features.

The present disclosure generally relates to compositions and methods for mitigating a tolerance effect from ingestion of cannabis-based medicines in human subjects, for example, subjects having an increased risk of unresponsiveness to one or more therapeutic agents such as, e.g., antidepressants and antianxiety drugs, or therapeutic agents containing THC, THCA, or an active analogue thereof, as active ingredient. In some embodiments, the human subjects have been previously treated with one or more therapeutic agents such as, e.g., antidepressants and antianxiety drugs, and have developed at least partial tolerance to the one or more therapeutic agents.

In one aspect, a method of mitigating a tolerance effect from ingestion of cannabis-based medicines in a subject is disclosed. The method includes (i) administering to the subject a therapeutically effective amount of a cannabis butter formulation; and (ii) administering to the subject a therapeutically effective amount of a $CO_2$ extract cannabis oil formulation.

Implementations of embodiments of the method according to the present disclosure can include one or more of the following features. In some embodiments, the tolerance effect comprises one or more deficits selected from the group consisting of deficits in hyperactivity, impulsivity and inattention including cognitive and behavioral impairments resulting therefrom; deficits in timing; deficits in social interaction; deficits in controlling repetitive behaviors; deficits in oral communication skills; deficits in motor skills; deficits in visual/spatial problem solving; deficits in sensory processing; and combinations of any thereof. In some embodiments, the tolerance effect is selected from the group consisting of anxiety, reduced ability to focus, depression, mood change, obsessive-compulsive tendency, ADHD-related symptoms, hypersensitivity to sensory input, deficits in fine motor skills, deficits in cognitive functions, or combinations of any thereof.

In some embodiments, the administering a therapeutically effective amount of a cannabis butter formulation comprises administering a first amount and a second amount in succession. In some embodiments, the first amount is equal to the second amount. In some embodiments, the administering a therapeutically effective amount of a $CO_2$ extract cannabis oil formulation comprises administering a third amount and a fourth amount in succession. In some embodiments, the third amount is equal to the fourth amount. In some embodiments, the cannabis butter formulation and/or the $CO_2$ extract cannabis oil formulation is an edible formulation selected from the group consisting of food formulations, nutraceutical formulations, and pharmaceutical formulations. In some embodiments, the food formulation is a food product selected from the group consisting of lozenges, candies, cookies, baked goods. In some embodiments, the cannabis butter formulation includes cannabis infused organic unsalted butter.

In some embodiments, the cannabis butter formulation or the $CO_2$ extract cannabis oil formulation is administered to the subject in multiple dosages, wherein each dosage includes from about 5 mg to about 500 mg of tetrahydrocannabinol (THC), or tetrahydrocannabinolic acid (THCA), or an active analogue thereof. In some embodiments, the cannabis butter formulation and/or the $CO_2$ extract cannabis oil formulation is administered to the subject in multiple dosages. In some embodiments, each dosage includes from about 10 mg to about 50 mg, from about 20 mg to about 40 mg, from about 25 mg to about 35 mg, or from about 30 mg to about 50 mg of tetrahydrocannabinol (THC), or tetrahydrocannabinolic acid (THCA), or an active analogue thereof. In some embodiments, the cannabis butter formulation and/or the $CO_2$ extract cannabis oil formulation is administered to the subject in multiple dosages, wherein each dosage includes from about 0.1 mg to about 10 mg of cannabidiol (CBD), or cannabidiolic acid (CBDA), or an active analogue thereof. In some embodiments, the cannabis butter formulation and/or the $CO_2$ extract cannabis oil formulation is administered to the subject in multiple dosages. In some embodiments, each dosage includes from about 0.5 mg to about 5 mg, from about 1 mg to about 4 mg, from about 2 mg to about 5 mg, from about 3 mg to about 10 mg, from about 5 mg to about 8 mg, or from about 3 mg to about 6 mg of cannabidiol (CBD), or cannabidiolic acid (CBDA), or an active analogue thereof. In some embodiments, the ratio of the amount of THC to the amount of CBD is of from about 100:1 to about 1:100. In some embodiments, the ratio of the amount of THC to the amount of CBD is of about 20:1.

In some embodiments of the methods disclosed herein, the cannabis butter formulation or the $CO_2$ extract cannabis oil formulation is administered to the subject in multiple dosages for a treatment period of about 1 day to the remaining lifetime of the subject. In some embodiments, the cannabis butter formulation or the $CO_2$ extract cannabis oil formulation is administered to the subject in multiple dosages for a treatment period of about 1 week to about 52 weeks. In some embodiments, the cannabis butter formulation or the $CO_2$ extract cannabis oil formulation is administered to the subject for at least 2, at least 3, at least 4, at least 5, or at least 10 consecutive dosages. In some embodiments, the cannabis butter formulation and the $CO_2$ extract cannabis oil formulation are administered to the subject in cycles, wherein each cycle comprises administering the cannabis butter formulation in 2, 3, 4, or 5 consecutive dosages, followed by administering of the $CO_2$ extract cannabis oil formulation in 2, 3, 4, or 5 consecutive dosages. In some embodiments, the cannabis butter formulation and/or the $CO_2$ extract cannabis oil formulation is administered in multiple dosages provided every 4-6 hours. In some embodiments, the method disclosed herein is consisting essentially of administering the cannabis butter formulation and the $CO_2$-extract cannabis oil formulation to the subject in cycles, wherein each cycle comprises administering the cannabis butter formulation in 2 or 3 consecutive dosages, 20-40 mg per dose, followed by administering of the $CO_2$-extract cannabis oil formulation in 2 or 3 consecutive dosages, 20-40 mg per dose. In some embodiments, the method disclosed herein is consisting essentially of administering the cannabis butter formulation and the $CO_2$-extract cannabis oil formulation to the subject in cycles, wherein each cycle includes administering the cannabis butter formulation in 3 consecutive dosages, 20-40 mg per dose, followed by administering of the $CO_2$-extract cannabis oil formulation in 2 consecutive dosages, 20-40 mg per dose. In some embodiments, the method consists of administering two or three consecutive amounts of a cannabis butter formulation followed by administering two to three consecutive amounts of a $CO_2$-extract cannabis oil formulation.

In some embodiments, the methods disclosed herein further include pre-selecting the subject as having an increased risk of unresponsiveness to one or more antidepressant. In some embodiments, the subject has been previously treated with one or more antidepressant, and has developed at least a partial tolerance to the antidepressant. In some embodiments, at least one of the one or more antidepressant is a selective serotonin reuptake inhibitors (SSRI) pharmaceutical is selected from the group consisting of cericlamine, citalopram, cyanodothiepin, dapoxetine, escitalopram, femoxetine, fluoxetine, fluoxetine hydrochloride, fluvoxamine, fluvoxamine maleate, ifoxetine, indalpine, litoxetine, paroxetine, paxil, pexeva, sertraline, serzone, trazodone, trazodone hydrochloride, and zimelidine. In some embodiments, the cannabis butter formulation and/or the $CO_2$ extract cannabis oil formulation is administered to the subject as a single therapeutic agent or in combination with one or more additional therapeutic agents or treatments. In some embodiments, at least one of the one or more additional therapeutic agents is an antidepressant. In some embodiments, the one or more additional therapeutic agents or treatments is selected from the group consisting of selective serotonin reuptake inhibitors (SSRIs), selective norepinephrine reuptake inhibitors (SNRIs), tricyclic antidepressants (TCAs), monoamine oxidase inhibitors (MAOIs), atypical antidepressants, and combinations of any thereof In one aspect, some embodiments relate to methods of treating a human with autism spectrum disorder (ASD) comprising, administering a therapeutically effective amount of tetrahydrocannabinol (THC) to the human. Some embodiments relate to methods of treating a human with Attention-Deficit/Hyperactivity Disorder (ADHD) comprising, administering a therapeutically effective amount of THC to the human. Some embodiments relate to methods of treating one or more deficits in a human with ASD comprising, administering a therapeutically effective amount of THC to the human. Some embodiments disclosed herein relate to methods of treating one or more deficits in a human with ADHD comprising, administering a therapeutically effective amount of tetrahydrocannabinol (THC) to the human. Some embodiments relate to methods of treating one or more of the conditions that commonly occur comorbidly with ADHD or ASD, comprising administering a therapeutically effective amount of tetrahydrocannabinol (THC) to the human. In some embodiments, administration can be, for example, oral administration as defined herein.

In one aspect, some embodiments disclosed herein relate to the use of tetrahydrocannabinol (THC) in the manufacture of a medicament for the treatment of autism spectrum disorder (ASD) in a patient. Some embodiments related to a composition comprising a therapeutically effective amount of tetrahydrocannabinol (THC) for use in the treatment of autism spectrum disorder (ASD). Some embodiments relate to the use of tetrahydrocannabinol (THC) in the manufacture of a medicament for the treatment of Attention-Deficit/ Hyperactivity Disorder (ADHD) in a patient. Some embodiments relate to a composition comprising a therapeutically effective amount of tetrahydrocannabinol (THC) for use in the treatment of Attention-Deficit/Hyperactivity Disorder (ADHD). Some embodiments relate to methods of treating one or more of the conditions that commonly occur comorbidly with ADHD or ASD comprising, administering a therapeutically effective amount of a composition comprising tetrahydrocannabinol (THC) to the human.

In some embodiments, a therapeutically effective amount of THC can further comprise a pharmaceutically acceptable excipient. In some embodiments, the administration of THC can further comprise administration of cannabidiol (CBD), caffeine, and other commonly-prescribed medicaments for the conditions, including without limitation selective serotonin reuptake inhibitors (SSRI). In some embodiments, administration of THC can be in the form of a capsule, caplet, tablet, an edible, or a liquid. In some embodiments, the capsule, caplet, tablet, or edible is a time-release capsule, caplet, tablet, or edible. In additional embodiments, the capsule, caplet, tablet, edible, or liquid comprises a dose of 0.001 mg/kg to 0.01 mg/kg, 0.01 mg/kg to 0.1 mg/kg, 0.1 mg/kg to 1 mg/kg, 1 mg/kg to 2 mg/kg, 2 mg/kg to 3 mg/kg, 3 mg/kg to 4 mg/kg, 4 mg/kg to 5 mg/kg, 5 mg/kg to 6 mg/kg, 6 mg/kg to 7 mg/kg, 7 mg/kg to 8 mg/kg, 8 mg/kg to 9 mg/kg, 9 mg/kg to 10 mg/kg, 10 mg/kg to 11 mg/kg, 11 mg/kg to 12 mg/kg, 12 mg/kg to 13 mg/kg, 13 mg/kg to 14 mg/kg, 14 mg/kg to 15 mg/kg, 15 mg/kg to 20 mg/kg, 20 mg/kg to 25 mg/kg, 25 mg/kg to 30 mg/kg, 30 mg/kg to 35 mg/kg, 35 mg/kg to 40 mg/kg, 40 mg/kg to 45 mg/kg, or more than 45 mg/kg, based on the human's weight.

In some embodiments, THC is administered to the human at a dose of 0.001 mg/kg to 0.01 mg/kg, 0.01 mg/kg to 0.1 mg/kg, 0.1 mg/kg to 1 mg/kg, 1 mg/kg to 2 mg/kg, 2 mg/kg to 3 mg/kg, 3 mg/kg to 4 mg/kg, 4 mg/kg to 5 mg/kg, 5 mg/kg to 6 mg/kg, 6 mg/kg to 7 mg/kg, 7 mg/kg to 8 mg/kg, 8 mg/kg to 9 mg/kg, 9 mg/kg to 10 mg/kg, 10 mg/kg to 11 mg/kg, 11 mg/kg to 12 mg/kg, 12 mg/kg to 13 mg/kg, 13 mg/kg to 14 mg/kg, 14 mg/kg to 15 mg/kg, 15 mg/kg to 20 mg/kg, 20 mg/kg to 25 mg/kg, 25 mg/kg to 30 mg/kg, 30 mg/kg to 35 mg/kg, 35 mg/kg to 40 mg/kg, 40 mg/kg to 45 mg/kg, or more than 45 mg/kg, based on the human's weight. In some embodiments, THC is administered to a human at a dose of 2.5 mg THC, 5 mg THC, 10 mg THC, 15 mg THC, 25 mg THC, 30 mg THC, from about 25 mg THC to about 35 mg THC, or from about 35 mg THC to about 50 mg of THC. some embodiments, THC is administered to a human at a dose of 1 mg to 5 mg, from 5 mg to 10 mg, from 10 mg to 20 mg, from 20 mg to 30 mg, from 30 mg to 40 mg, from 40 mg to 50 mg, from 50 mg to 60 mg, from 60 mg to 70 mg, from 70 mg to 80 mg, from 80 mg to 90 mg, from 90 mg to 100 mg, from 100 mg to 110 mg, from 110 mg to 120 mg, from 120 mg to 130 mg, from 130 mg to 140 mg, from 140 mg to 150 mg, from 150 mg to 200 mg, from 200 mg to 250 mg, from 250 mg to 300 mg, from 300 mg to 350 mg, from 350 mg to 500 mg, from 500 mg to 1,000 mg, or 1,000 mg or above of THC.

In some embodiments, THC is administered one time per day, two times per day, three times per day, four times per day, five times per day, or six or more times per day. In some embodiments, the human is 3-17 years old, or 18 years old or above. In some embodiments, in addition to treating ASD, one or more comorbid symptoms, disorders, or conditions is also treated. In some embodiments, in addition to treating ADHD, one or more comorbid symptoms, disorders, or conditions is also treated. In some embodiments, certain comorbid symptoms and disorders are treated even absent a concurrent diagnosis with ASD or ADHD.

In some embodiments, a deficit in a human with autism spectrum disorder (ASD) can be: a deficit in social communication, social interaction, or a restrictive or repetitive pattern of behavior, interest, or activity; or the deficit is in social communication, oral communication, social interaction, interpreting body language, nonverbal communication, developing, maintaining, or understanding relationships, social-emotional reciprocity, restrictive behavior, repetitive thought, repetitive behavior, inattention, hyperactivity, impulsivity, sensory processing, timing, motor timing, perceptual timing, temporal foresight, time estimation, motor skills, or visual/spatial problem solving. In some embodiments, in addition to treating one or more deficits associated with ASD, one or more comorbid symptoms, disorders, or conditions is also treated.

In some embodiments, a deficit in a human with Attention-Deficit/Hyperactivity Disorder (ADHD) can be: a deficit in inattention, hyperactivity, or impulsivity; or a deficit in social communication, oral communication, social interaction, interpreting body language, nonverbal communication, developing, maintaining, or understanding relationships, social-emotional reciprocity, restrictive behavior, repetitive thought, repetitive behavior, inattention, hyperactivity, impulsivity, sensory processing, timing, motor timing, perceptual timing, temporal foresight, time estimation, motor skills, or visual/spatial problem solving. In some embodiments, in addition to treating one or more deficits associated with ADHD, one or more comorbid symptoms, disorders, or conditions is also treated.

In one aspect, some embodiment disclosed herein relate to a method of treating a human with autism spectrum disorder (ASD), comprising administering a therapeutically effective amount of tetrahydrocannabinol (THC) to the human. In some embodiments of this method, in addition to treating ASD, one or more comorbid symptoms, disorders, or conditions is also treated. In some embodiments, the one or more comorbid symptoms is anxiety, depression, obsessive-compulsive disorder (OCD), substance abuse, or a combination of any thereof.

In one aspect, some embodiment disclosed herein relate to a method of treating one or more deficit in a human with autism spectrum disorder (ASD), including administering a therapeutically effective amount of a tetrahydrocannabinol (THC) to the human. In some embodiments, the one or more deficit is in social communication, social interaction, or a restrictive or repetitive pattern of behavior, interest, or activity.

In another aspect, some embodiments disclosed herein relate to a method of treating one or more deficit in a human with Attention-Deficit/Hyperactivity Disorder (ADHD), including administering a therapeutically effective amount of tetrahydrocannabinol (THC) to the human. In some embodiments, the one or more deficit is in inattention, hyperactivity, or impulsivity, including any associated cognitive, behavioral and motor impairments arising therefrom. In some embodiments of this aspect and other aspects of the disclosure, the one or more deficit is social communication, oral communication, social interaction, interpreting body language, nonverbal communication, developing, maintaining, or understanding relationships, social-emotional reciprocity, restrictive behavior, repetitive thought, repetitive behavior, inattention, hyperactivity, impulsivity, sensory processing, timing, motor timing, perceptual timing, temporal foresight, time estimation, motor skills, or visual/spatial problem solving. In some embodiments, the method according to this aspect and other aspects of the disclosure further includes administration of cannabidiol (CBD), caffeine, a selective serotonin reuptake inhibitor (SSRI), or a combination of any thereof.

In a related aspect of the disclosure, some embodiments described herein relate to a composition comprising a therapeutically effective amount of tetrahydrocannabinol (THC) for use in the treatment of autism spectrum disorder (ASD) and/or Attention-Deficit/Hyperactivity Disorder (ADHD).

The foregoing summary is illustrative only and is not intended to be in any way limiting. In addition to the illustrative embodiments and features described herein, further aspects, embodiments, objects and features of the application will become fully apparent from the drawings and the detailed description and the claims.

DETAILED DESCRIPTION OF CERTAIN INVENTIVE EMBODIMENTS

The following detailed description is provided to aid those skilled in the art in practicing the present disclosure. Even so, this detailed description should not be construed to unduly limit the present disclosure as modifications and variations in the embodiments discussed herein can be made by those of ordinary skill in the art without departing from the spirit or scope of the present discovery.

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

Some Definitions

As used in this disclosure and the appended claims, the singular forms "a", "an" and "the" include a plural reference unless the context clearly dictates otherwise. For example, the term "a therapeutic agent" includes one or more therapeutic agents, comprising mixtures thereof. As used in this disclosure and the appended claims, the term "or" can be singular or inclusive. For example, "A or B" can be A and B. "A and/or B" may also be used herein to include all of the following alternatives: "A", "B", "A or B", and "A and B".

"About" means either within plus or minus 10% of the provided value, or rounded to the nearest significant figure, in all cases inclusive of the provided value. Where ranges are provided, they are inclusive of the boundary values.

The terms "administration" and "administering", as used herein, refer to the delivery of a bioactive composition or formulation by an administration route comprising, but not limited to, oral, intravenous, intra-arterial, intramuscular, intraperitoneal, subcutaneous, intramuscular, and topical administration, or combinations thereof.

As used herein, "cannabis extract" or "cannabis oil" refers to a substance obtained by extracting a raw cannabis plant material, using a solvent, wherein the solvent has substantially been removed. In some embodiments, the process of extracting a raw cannabis plant material using a solvent includes a hot solvent extraction. In some embodiments, the process of extracting a raw plant material using a solvent includes supercritical fluid extraction (SFE), such as, e.g., $CO_2$. In reference to Cannabis, suitable extracts include, e.g., kief, hash, bubble hash, solvent-reduced oil, tincture, e-juice, or combination thereof. In some embodiments, the cannabis extract can be further enriched with certain desired chemical compounds (e.g., cannabinoids, terpenes, terpenoids, and/or flavonoids).

The phrase "cannabis-based composition" or "cannabis-based formulation" refers to a composition or formulation having has at least one active ingredient which is a cannabis extract or an active cannabis-derived chemical compound such as, cannabinoids, terpenes, terpenoids, and/or flavonoids. As such, the phrase "cannabis-based formulation" encompasses food, beverage, nutraceuticals, medicines, and pharmaceutical formulations in which at least one of the active ingredients is a cannabis extract or an active chemical compound derived from cannabis. In some embodiments, the cannabis-based formulation is a formulation comprising THC, THCA, or an active analogue as an active ingredient. In some embodiments, the cannabis-based formulation is a formulation comprising CBD, CBDA, or an active analogue as an active ingredient.

The term "edible consumable" means a food, beverage, or an ingredient of a food or beverage suitable for human or animal consumption.

As used herein, the term "plant" refers to plants in the genus of Cannabis and plants derived thereof. Suitable plants can include Cannabis plants produced via asexual reproduction and via seed production. The term "plant part" refers to any part of a plant including, but not limited to, organelles, single cells and cell tissues such as plant cells that are intact in plants, cell clumps and tissue cultures from which cannabis plants can be regenerated. Examples of plant parts include, but are not limited to, single cells and tissues from pollen, ovules, leaves, embryos, roots, root tips, tubers, anthers, flowers, fruits, stems shoots, and seeds; as well as pollen, ovules, leaves, embryos, roots, root tips, anthers, flowers, fruits, stems, shoots, scions, rootstocks, seeds, tubers, protoplasts, and calli. The two main parts of plants grown in some sort of media, such as soil, are often referred to as the "above-ground" part, often referred to as the "shoots", and the "below-ground" part, often referred to as the "roots". The term "*Cannabis* plant material" is to be interpreted as encompassing plant material derived from one or more *Cannabis* plants.

The term "therapeutic agent" refers to a chemical substance, such as a medicinal, pharmaceutical, nutraceutical agent, that is used to treat a health condition, particularly a tolerance effect caused by ingestion of a cannabis-based formulation.

As used herein, the terms "treating" and "treatment" refer to delaying the onset of, retarding or reversing the progress of, reducing the severity of, or alleviating or preventing either the disease, pathology, or health condition to which the term applies, or one or more symptoms of such disease, pathology, or health condition. It also applies to diseases, pathologies, or health conditions with normal responsiveness to a therapeutic agent but which will benefit from the treatment. The term "mitigating" refers to reduction, inhibition, or elimination of one or more symptoms of that health condition, pathology, or disease, and/or a reduction in the rate or delay of onset or severity of one or more symptoms of that health condition, pathology, or disease, and/or the prevention of that health condition pathology, or disease.

As used herein the terms "combination" and "in combination with" mean the administration of a therapeutic formulation described herein together with at least one additional therapeutic or medicinal agent (e.g., an antidepressant agent), potentially either sequentially or simultaneously. For example, the term encompasses dosing simultaneously, or within minutes or hours of each other, or on the same day, or on alternating days, or dosing the therapeutic formulation described herein on a daily basis, or multiple days per week, or weekly basis, for example, while administering another substance such as a therapeutic agent on the same day or alternating days or weeks or on a periodic basis during a time simultaneous therewith or concurrent therewith, or at least a part of the time during which the therapeutic formulation described herein is dosed.

As will be understood by one having ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

In the methods or processes described herein, the steps can be carried out in any order without departing from the principles of the inventive methods disclosed herein, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

As used herein, "comprising" is synonymous with "including," "containing," or "characterized by," and is inclusive or open-ended and does not exclude additional, unrecited elements or method steps. As used herein, "consisting of" excludes any elements, steps, or ingredients not specified in the claimed composition or method. As used herein, "consisting essentially of" does not exclude materials or steps that do not materially affect the basic and novel characteristics of the claimed composition or method. Any recitation herein of the term "comprising", particularly in a description of components of a composition or in a description of steps of a method, is understood to encompass those compositions and methods consisting essentially of and consisting of the recited components or steps.

Headings, e.g., (a), (b), (i) etc., are presented merely for ease of reading the specification and claims. The use of headings in the specification or claims may not necessarily require the steps or elements be performed in alphabetical or numerical order or the order in which they are presented, unless it is expressly indicated.

Methods of the Disclosure

In one aspect, a method of mitigating a tolerance effect from ingestion of cannabis-based formulations in a subject is disclosed. The method includes (i) administering to the subject a therapeutically effective amount of a cannabis butter formulation; and (ii) administering to the subject a therapeutically effective amount of a $CO_2$-extract cannabis oil formulation.

In principle, methods according to the present disclosure can include formulations containing extracts derived from plant materials of any plant species belonging to the genus *Cannabis*. Non-limiting examples of suitable *Cannabis* species include *Cannabis sativa, Cannabis indica*, and *Cannabis ruderalis*. Hybrid cannabis strains and inbred cannabis strains are both suitable. Accordingly, in some embodiments, the cannabis-based formulations disclosed herein can include extracts from a hybrid cannabis strain. In some embodiments, the cannabis-based formulations can include extracts from a inbred cannabis strain. In some embodiments, the cannabis-based formulations can include extracts from plant materials of one or more varieties of whole *Cannabis* plants, particularly *Cannabis sativa, Cannabis indica, Cannabis ruderalis*, or plants which are the result of genetic crosses, self-crosses or hybrids thereof. Non-limiting examples of suitable strains of *Cannabis* include, Blueberry, White Widow, Charlotte's Web, Diesel, Haze, BC Bud, Holland's Hope, Kush, Northern Lights, Purple, Jack Herer, Acapulco Gold and Malawi Gold (Chamba), Shaman, Sour, Skunk, and Te Puke Thunder. Further examples of suitable *Cannabis* strains include, but are not limited to Blackberry Kush, Blue Dream, Bubba Kush, Cherry Pie, Durban Poison, Fire OG, Girl Scout Cookies, Gorilla Glue, Grape Ape, Green Crack, Headband, Kosher Kush, Master Kush, OG Kush, Purple Haze, Purple Kush, Skywalker OG, Sour Diesel, Super Lemon Haze, Super Silver Haze, and White Widow. Additional non-limiting examples of preferred Cannabis strains include strains that have been deposited under NCIMB Nos. 41541, 42254, 42255, 42256, 42257, and 42258. In some embodiments, the cannabis-based formulations can include extracts from any physical part of the plant materials. Suitable plant materials include, but are not limited to, e.g., the leaf, bud, flower, trichome, seed, or a combination thereof.

The *Cannabis* plant material contains suitable and desirable compounds, useful in the pharmaceutical dosage forms and methods of medical treatment described herein. Cannabinoids, terpenoids, and flavonoids are included amongst the various suitable and desirable compounds. Accordingly, in some embodiments, the cannabis butter formulation and/or the $CO_2$ extract cannabis oil formulation can include one or more cannabis-derived cannabinoid compounds. Cannabinoids are the most studied group of secondary metabolites in *Cannabis*. Most exist in two forms, as acids and in neutral forms (e.g., decarboxylated forms). The acid form is designated by an "A" at the end of its acronym (e.g., THCA). The phytocannabinoids are synthesized in the plant as acid forms, and while some decarboxylation does occur in the plant, it increases significantly post-harvest and the kinetics increase at high temperatures. In general, decarboxylation can be achieved by thorough drying of the cannabis plant material followed by heating it, often by combustion, vaporization, or heating or baking in an oven. Unless otherwise noted, references to cannabinoids in a plant include both the acidic and decarboxylated versions (e.g., THC and THCA).

Typical cannabinoids isolated from *Cannabis* plants include, but are not limited to, tetrahydrocannabinol (THC), cannabidiol (CBD) and cannabinol (CBN). Other cannabinoids include for example, cannabichromene (CBC), cannabigerol (CBG) cannabinidiol (CBND), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM). As used herein THC, CBD, CBN, CBC, CBG, CBND, CBL, CBV, THCV, CBDV, CBCV, CBGV and CBGM refer to the decarboxylated form of the cannabinoid. Whereas, THCA, CBDA, CBNA, CBCA, CBGA, CBNDA, CBLA, CBVA, THCVA, CBDVA, CBCVA, CBGVA and CBGAM (cannabigerolic acid monomethyl ether) refer to the corresponding acid form of the cannabinoid. In the *Cannabis* plant, cannabinoids are synthesized and accumulated as cannabinoid acids (e.g., cannabidiolic acid (CBDA)). When the herbal product is dried, stored, or heated, the acids are decarboxylated gradually or completely into neutral forms (e.g., THCA→THC and CBDA→CBD).

Accordingly, in some embodiments, the cannabis butter formulation and/or the $CO_2$-extract cannabis oil formulation can include at least two, at least three, at least four, at least five, at least six, at least seven, at least eight, at least nine, at least ten, at least eleven, or at least twelve cannabis-derived cannabinoid compounds. In some embodiments, the one or more cannabis-derived cannabinoid compounds is selected from the group consisting of THC, CBD, CBN, CBC, CBG, CBND, CBL, CBV, THCV, CBDV, CBCV, CBGV, CBGM, THCA, CBDA, CBNA, CBCA, CBGA, CBNDA, CBLA, CBVA, THCVA, CBDVA, CBCVA, CBGVA,CBGAM, and combinations of any thereof. In some embodiments, the cannabis butter formulation and/or the $CO_2$-extract cannabis oil formulation can include THC (or THCA or an active analogue thereof). In some embodiments, the cannabis butter formulation and/or the $CO_2$-extract cannabis oil formulation can include CBD (or CBDA or an active analogue thereof). In some embodiments, the methods and compositions as described herein can exclude one or more of the cannabis-derived cannabinoid compounds described above. In some particular embodiments, the methods and compositions disclosed herein specifically exclude THC. In some particular embodiments, the methods and compositions disclosed herein specifically exclude CBD. In some embodiments, the compositions and methods disclosed herein specifically exclude cannabinoids (i.e., no cannabinoid is present).

Tetrahydrocannabinol (THC) is the primary psychoactive component of the *Cannabis* plant. THC has been generally considered to be only psychoactive in is decarboxylated state (THC), while the carboxylic acid form (THCA) is non-psychoactive. In particular, delta-9-tetrahydrocannabinol (Δ9-THC, THC) and delta-8-tetrahydrocannabinol (Δ8-THC) mimic the action of anandamide, a neurotransmitter produced naturally in the body. These two THCs produce the effects associated with cannabis by binding to the CB1 cannabinoid receptors in the brain. THC appears to ease moderate pain (analgesic) and to be neuroprotective, while also offering the potential to reduce neuro-inflammation and to stimulate neurogenesis. THC has approximately equal affinity for the CB1 and CB2 receptors. In some embodiments, the cannabis butter formulation and/or the $CO_2$ extract cannabis oil formulation described herein includes dronabinol, nabilone, or a combination thereof. In some embodiments, the cannabis butter formulation and/or the $CO_2$ extract cannabis oil formulation described herein includes Marinol®.

Cannabidiol ("CBD") is another major cannabinoid constituent of the plant which typically represents up to 40% in its extracts. CBD has been shown to reduce and modulate the psychoactivity of THC and also reduce some of THC's psychoactive and other effects, which can include tachycardia, anxiety, etc. There is some evidence that CBD may reduce the buildup of tolerance to the effects of THC and also reduce the likelihood of *Cannabis* dependency. Compared with THC, CBD is not psychoactive in healthy individuals, and is considered to have a wide scope of medical applications, including to epilepsy, multiple sclerosis spasms, anxiety disorders, bipolar disorder, schizophrenia, nausea, convulsion and inflammation, as well as inhibiting cancer cell growth. CBD was generally believed not to affect the psychoactivity of THC. However, recent evidence shows that smokers of cannabis with a higher CBD/THC ratio were less likely to experience schizophrenia-like symptoms. This observation is supported by psychological tests, in which participants experience less intense psychotic-like effects when intravenous THC was co-administered with CBD (as measured with a PANSS test). CBD has little affinity for CB1 and CB2 receptors but acts as an indirect antagonist of cannabinoid agonists. Recently it was found to be an antagonist at the putative new cannabinoid receptor, GPR55, a GPCR expressed in the caudate nucleus and putamen. CBD has also been shown to act as a 5-HT1A receptor agonist, an action that is involved in its antidepressant, anxiolytic, and neuroprotective effects. CBD has been reported to relieve convulsion, inflammation, anxiety, and nausea. CBD has a greater affinity for the CB2 receptor than for the CB1 receptor. CBD shares a precursor with THC and is the main cannabinoid in low-THC *Cannabis* strains. CBD has also been reported to plays a role in preventing the short-term memory loss associated with THC in mammals.

As used herein, "cannabis extract" or "cannabis oil" refers to a substance obtained by extracting a raw cannabis plant material using a solvent, wherein the solvent has substantially been removed. In some embodiments, the process of extracting a raw cannabis plant material using a solvent includes a hot solvent extraction. In some embodiments, the process of extracting a raw cannabis plant material using a solvent includes supercritical fluid extraction (SFE), such as, e.g., $CO_2$. In reference to *Cannabis*, suitable extracts can include, e.g., kief, hash, bubble hash, solvent-reduced oil, tincture, e-juice, or combination thereof. In some embodiments, the cannabis extract can be further enriched with certain desired chemical compounds (e.g., cannabinoids, terpenes, terpenoids, and/or flavonoids).

The precise cannabinoid content of any particular cannabis variety can be qualitatively and quantitatively determined using methods well known to those skilled in the art, such as TLC or HPLC. Thus, one can chose a *Cannabis* variety from which to prepare an extract which will produce the desired cannabinoid ratios such as, for example, the ratio of THC to CBD. Alternatively, extracts from two of more different *Cannabis* varieties can be mixed or blended to produce a material with the preferred cannabinoid ratio for formulating into a desired formulation.

Cannabinoids may be present in cannabis biomass as free cannabinoids and as the corresponding acidic precursors. Conventional methods of cannabis extract preparation typically involve the total extraction of free cannabinoids and precursors with solvents such as lower alkyl alcohols, particularly methanol. More recently, several extraction techniques and systems have been developed to prepare cannabis extracts. A number of such recent extraction techniques involve the use of organic solvents alone (e.g., ethyl alcohol, propane, butane, and the like), or a lipid-based solvent (such as oil or butter), or in admixture with water and under sub-critical or supercritical conditions (such as $CO_2$).

Current cannabis oil extraction techniques generally fall into two categories: heat-extraction techniques (solvent such as oil, e.g. butter extraction) and unheated-extraction techniques (e.g. under sub-critical or supercritical conditions). In unheated-extraction techniques, the extraction process is carried out at a very low temperature, and the end product (e.g. cannabis extract) is composed primarily the acidic form of THC and CBD (i.e. THCA and CBDA, respectively). *Cannabis* extracts produced via unheated-extraction techniques have specialized properties and effects on receptors, thus providing unique medicinal properties which can be deployed in treating a variety of medical conditions. In particular, mammalian tissues contain two types of cannabinoid receptors that have been identified, CB1 and CB2. CB1 receptors are expressed mainly by neurons of the central and peripheral nervous system (CB1cns and CB1pns). CB2 receptors are located on non-neuronal tissues, particularly on immune cells throughout the body. Without being bound to any particular theory, cannabis extracts produced via unheated-extraction techniques have more affinity for the CB2 receptors. Its action is focused on the peripheral receptors that modulate pain and inflammation. The CB2 receptors are located on immune cells of the body and as such when stimulated act to inhibit, evoke immune cell migration and modulate cytokine release. The action on these receptors may act to produce an anti-nociception effect through the suppression of inflammatory mediators. Additionally there appear to be other effects on the immune system through stimulation of the CB2 receptors. It has been reported that the action on the CB2 receptors is effected by one of the non-psychoactive cannabinoid extracts from the whole plant. This main non-psychoactive compound is delta-9-tetrahydrocannabinol acid (THCA) that acts to affect the immune system through its ability to inhibit tumor necrosis factor alpha (TCF-alpha).

On the other hand, the high-temperatures used during heated-extraction techniques decarboxylates the inactive cannabinoids, such as THCA, and convert it into the active form, such as THC. Therefore, cannabis extracts produced via heated-extraction techniques contain a key ingredient of a decarboxylated form of THC, and selectively stimulates the CBcns receptor sites located in the brain, such as CB1 receptors located in the central nervous system. In particular, the psychoactive effect of cannabis is reportedly mediated by selective stimulation of the CB1cns receptors. This action is produced by agonistic actions on these G protein coupled receptor sites in the central nervous system. Without being bound to any particular theory, the major active ingredient in the cannabis extract that acts agonistically on the CB1cns receptors is generally reported to be the decarboxylated form delta-9-tetrahydrocannabinol.

Accordingly, in some embodiments, the method includes a step of preparing cannabinoid-rich extract from cannabis plant material. In some embodiments, the method includes providing fresh or live cannabis plant material; and extracting the cannabinoids from the fresh or live plant material to produce the cannabinoid-rich extract. Optionally, the method includes decarboxylating the cannabinoids prior the extraction step. In some embodiments, the method includes decarboxylating the cannabinoids after the extraction step.

In some embodiments, the cannabis extracts described herein can be formulated with one or more pharmaceutically acceptable carriers, diluents or excipients or deposited on a pharmaceutically acceptable surface for vaporization in order to produce pharmaceutical formulations containing one or more cannabinoids, such as THC, THCA, CBD, and/or CBDA, as the pharmaceutically active agents.

In some embodiments, separate cannabis extracts can be prepared from single *Cannabis* plant varieties having differing cannabinoid content (e.g. high THC and/or high CBD plants) and then mixed or blended together prior to formulation to produce the final pharmaceutical formulations. This approach is preferred if, for example, it is desired to achieve a defined ratio by weight of individual cannabinoids in the final formulations. Alternatively, plant material from one or more *Cannabis* plant varieties of defined cannabinoid content can be mixed together prior to extraction of a single botanical drug substance having the desired cannabinoid content, which can then be formulated into a final pharmaceutical formulation.

The phrase "cannabis-based formulation", as used herein, refers to a composition or formulation having at least one active ingredient which is a cannabis extract or an active cannabis-derived chemical compound such as, cannabinoids, terpenes, terpenoids, and/or flavonoids. As such, the phrase "cannabis-based formulation" encompasses food, beverage, nutraceuticals, medicines, and pharmaceutical formulations in which at least one of the active ingredients is a cannabis extract or an active chemical compound derived from cannabis. In some embodiments, the cannabis-based formulation is a formulation comprising THC, THCA, or an active analogue as an active ingredient. In some embodiments, the cannabis-based formulation is a formulation comprising CBD, CBDA, or an active analogue as an active ingredient. In some embodiments, the cannabis extracts can be incorporated into an edible formulation. The term "edible formulation," as used herein, means a food, beverage, or an ingredient of a food or beverage suitable for human or animal consumption. Non-limiting examples of edible formulations include such as, for example, foods, beverages, pharmaceuticals, nutraceuticals, and the like, which are suitable for human and/or animal consumption. In some particular embodiments, the food formulation can be a food product selected from the group consisting of lozenges, candies, cookies, and baked goods.

*Cannabis* Butter Formulation

In some embodiments, the cannabis-based formulation described herein can be a "cannabis butter formulation", which is typically a butter-based composition in which butter has been infused with cannabis-derived chemical compounds. In these instances, the cannabis extract or cannabis oil can be obtained by a lipid-based extraction method which includes marinating *Cannabis* flower tissues in a lipophilic solvent such as, for example butter, for a suitable time period, followed by straining off the flower tissues. This method uses butter as an extraction agent.

In some embodiments, the cannabis butter formulation can take a shape and/or a form of baked goods such as, a cookie, suitable for oral administration. In these instances, active ingredients of the cannabis butter formulation can be absorbed to users' body primarily by sublingual administration and digestive tract. In some embodiments, in addition to the two active ingredients, CBD and THC, the cannabis butter formulation can include one or more additional ingredients. Suitable additional ingredients include, but are not limited to, cane sugar, syrup, salt, filtered water, baking soda, baking powder, natural flavoring, natural colorings, which contribute to the volume and/or weight, shape, color, taste, texture, and hardness of the cannabis butter formulation (e.g., cookie). In some particular embodiments, as described in more detail in Example 4 below, the cannabis butter formulation takes form and shape of a cookie which includes *Cannabis* infused organic unsalted butter and one or more of the following ingredients: organic cane sugar, sea salt, fair-trade organic chocolate, organic cocoa liquor, organic cane sugar, organic cocoa butter, organic natural cocoa powder, pasteurized sweet cream, lactic acid, baking soda, baking powder, organic all-purpose flour, and organic vanilla.

$CO_2$-extract *Cannabis* Oil Formulation

In some embodiments disclosed herein, the cannabis-based formulation described herein can be a "$CO_2$-extract cannabis oil formulation". In these instances, the cannabis extract or cannabis oil can be prepared by a supercritical fluid extraction process wherein carbon dioxide ($CO_2$) used as a supercritical fluid. Without being bound to any particular theory, this is because carbon dioxide is generally considered to be a safe, non-toxic material that occurs in nature, and $CO_2$ used in a processing step can be completely removed from a final clean product without leaving essentially any residue behind.

In some embodiments, the $CO_2$-extract cannabis oil formulation of the methods disclosed herein can take shape and form of a conventional lozenge tablet or a hard candy or crumble. In some embodiments, when the $CO_2$-extract cannabis oil formulation is in the lozenges format, users can split individual tablet(s) from a lozenge bar, according to the dosage desired. In some embodiments, the $CO_2$-extract cannabis formulation can be made into a candy format such as an individual drop, a lollipop, or crumble. Regardless of formats, the $CO_2$-extract cannabis oil formulation can be administered orally. For example, users can leave the $CO_2$-extract cannabis oil formulation in their mouth and let it dissolve naturally or ingest it, or both. In some embodiments, active ingredients of the $CO_2$-extract cannabis oil formulation can be absorbed to users' body primarily by sublingual administration and digestive tract.

In some embodiments, if desired, one can enhance the efficiency of delivery of active ingredients of the $CO_2$-extract cannabis oil formulation by modulating the size, shape, solubility and hardness of the $CO_2$-extract cannabis oil formulation. Accordingly, in some embodiment, the $CO_2$-extract cannabis oil formulation can be made in regular lozenge size for ease of consumption. In some embodiment, in addition to the two active ingredients, CBD and THC, the $CO_2$-extract cannabis oil formulation can include one or more additional ingredients. Suitable additional ingredients include, but are not limited to, cane sugar, syrup, filtered water, natural organic flavoring, Xylitol, coconut oil (which can be raw and/or organic coconut oil), natural organic colorings, which contribute to the volume and/or weight, shape, color, taste, texture, hardness and solubility of the $CO_2$-extract cannabis oil formulation (e.g., candy or lozenge). In some embodiments, as described in more detail in Example 5 below, the $CO_2$-extract cannabis oil formulation can take form and shape of a hard candy or lozenge which includes one or more of the following ingredients: organic cane sugar, organic light corn syrup, reverse osmosis water, organic gum acacia, organic flavors and colors made from organic fruit and vegetable extracts, and sea salt.

In various embodiments, the cannabis extracts as described herein can be formulated with any convenient pharmaceutically acceptable diluents, carriers or excipients to produce a pharmaceutical composition. The choice of diluents, carriers or excipients will depend on the desired dosage form, which may in turn be dependent on the intended route of administration to a patient. Such dosage forms can be prepared in accordance with standard principles of pharmaceutical formulation, known to those skilled in the art.

In some embodiments, the cannabis-based formulation described herein, or an edible product derived therefrom, is administered at a therapeutically effective amount to the subject. As used herein, the term "therapeutically effective amount" means that amount of the formulation or formulations being administered which will relieve to some extent one or more of the symptoms of the health condition being treated. In reference to the treatment of a tolerance effect from ingestion of cannabis-based formulations, a therapeutically effective amount refers to that amount which has the effect of reducing, relieving, inhibiting, or preferably eliminating one or more symptoms or deficits associated with the ingestion of a cannabis-based formulation. In some embodiments, the one or more symptoms or deficits are associated with a condition that returns or recurs on account of developing a tolerance to a THC-containing drug or treatment. In some embodiments, the tolerance effect can involve recurrence of one or more deficits in hyperactivity, deficits impulsivity and inattention including cognitive and behavioral impairments resulting therefrom; deficits in timing; deficits in social interaction; deficits in controlling repetitive behaviors; deficits in oral communication skills; deficits in motor skills; deficits in visual/spatial problem solving; deficits in sensory processing. In some embodiments, the tolerance effect includes a combination of any of the foregoing deficits.

Generally, baseline measures of deficits and symptoms can be obtained through reports from patients and other sources including, for example, families, therapists, physicians, caretakers and teachers. Baseline measures of symptoms and deficits can also be obtained using currently-accepted diagnostic procedures, including without limitation those tests specifically identified above. Baseline measures in deficits and symptoms can also be obtained through observation of the patient engaging in routine daily activities such as walking, speaking and otherwise interacting with others, as well as observation of the patient performing tasks requiring fine-motor skills such as threading a needle, drawing, or writing in cursive.

After an adjustment period of approximately 1-2 weeks to allow the subjects to acclimate to the effects of the cannabis-based formulations described herein, the subjects should exhibit fewer and less severe tolerance effect-related symptoms and deficits and, in particular, should experience fewer and less severe manifestations of the symptoms and deficits identified above.

In some embodiments, the administering a therapeutically effective amount of a cannabis butter formulation comprises administering a first amount and a second amount in succession. In some embodiments, the first amount and a second amount can be different. In some embodiments, the first amount is equal to the second amount. In some embodiments, the administering a therapeutically effective amount of a $CO_2$ extract cannabis oil formulation comprises administering a third amount and a fourth amount in succession. In some embodiments, the third amount is different from the fourth amount. In some embodiments, the third amount is equal to the fourth amount.

In some embodiments of the methods disclosed herein, the cannabis butter formulation and/or the $CO_2$ extract cannabis oil formulation is administered to the subject in a single dose. In some embodiments, the cannabis butter formulation and/or the $CO_2$ extract cannabis oil formulation is administered to the subject in multiple dosages. In some embodiments, the dosages are equal to one another. In some embodiments, the dosages are different from one another. In some embodiments, the cannabis butter formulation and/or the $CO_2$ extract cannabis oil formulation is administered in gradually increasing dosages over time. In some embodiments, the cannabis butter formulation and/or the $CO_2$ extract cannabis oil formulation is administered in gradually decreasing dosages over time.

Generally, one or more cannabinoid compounds can be incorporated in the cannabis-based formulations of the present disclosure in any suitable concentrations, which can be determined based on requirements of specific end applications. Accordingly, in some embodiments, the cannabis butter formulation and/or the $CO_2$ extract cannabis oil formulation is administered to the subject in a single dose which includes tetrahydrocannabinol (THC), or tetrahydrocannabinolic acid (THCA), or an active analogue thereof, in an amount ranging from about 10 mg to about 50 mg, from about 20 mg to about 40 mg, from about 25 mg to about 35 mg, or from about 30 mg to about 50 mg. In some embodiments, the cannabis butter formulation and/or the $CO_2$ extract cannabis oil formulation is administered to the subject in multiple dosages, wherein each dosage includes from about 5 mg to about 500 mg of tetrahydrocannabinol (THC), or tetrahydrocannabinolic acid (THCA), or an active analogue thereof. In some embodiments, the cannabis butter formulation and/or the $CO_2$ extract cannabis oil formulation is administered to the subject in multiple dosages, wherein each dosage includes from about 10 mg to about 50 mg, from about 20 mg to about 40 mg, from about 25 mg to about 35 mg, or from about 30 mg to about 50 mg of THC, or THCA, or an active analogue thereof. In some embodiments, the cannabis butter formulation and/or the $CO_2$ extract cannabis oil formulation described herein includes synthetic THC, dronabinol, nabilone, or a combination thereof. In some embodiments, the cannabis butter formulation and/or the $CO_2$ extract cannabis oil formulation described herein includes Marinol®.

In some embodiments, the cannabis butter formulation and/or the $CO_2$ extract cannabis oil formulation is administered to the subject in a single dose which includes cannabidiol (CBD), or cannabidiolic acid (CBDA), or an active analogue thereof, in an amount ranging from about 0.1 mg to about 10 mg, 0.5 mg to about 5 mg, from about 1 mg to about 4 mg, from about 2 mg to about 5 mg, from about 3 mg to about 10 mg, from about 5 mg to about 8 mg, or from about 3 mg to about 6 mg. In some embodiments, the cannabis butter formulation and/or the $CO_2$ extract cannabis oil formulation is administered to the subject in multiple dosages, wherein each dosage includes from about 0.1 mg to about 10 mg of CBD, or CBDA, or an active analogue thereof. In some embodiments, the cannabis butter formulation and/or the $CO_2$ extract cannabis oil formulation is administered to the subject in multiple dosages, wherein each dosage includes from about 0.5 mg to about 5 mg, from about 1 mg to about 4 mg, from about 2 mg to about 5 mg, from about 3 mg to about 10 mg, from about 5 mg to about 8 mg, or from about 3 mg to about 6 mg of CBD, or CBDA, or an active analogue thereof.

In some embodiments, the cannabis butter formulation and/or the $CO_2$ extract cannabis oil formulation described herein includes a specific ratio of the amount of CBD (or CBDA or an active analogue thereof) to the amount of THC (or THCA or an active analogue thereof). One skilled in the art can select a *Cannabis* variety from which to prepare an extract which will produce the desired cannabinoid ratios such as, for example, the ratio of THC to CBD. Alternatively, extracts from two of more different *Cannabis* varieties can be mixed or blended to produce a material with the preferred cannabinoid ratio for formulating into a desired formulation. In addition or alternatively, when CBD and THC cannot be extracted individually from concentrated cannabis oil or extract, sometimes mixing of various batches of concentrated cannabis oil or extract is required to achieve a mixture that has the desirable CBD:THC ratio. However, in some embodiments, separation of the CBD from the THC is possible, and then blending of THC and CBD to attain the optimum ration of CBD to THC can be achieved more efficiently but with the same result. In some embodiments, the ratio of the amount of THC (or THCA or an active analogue thereof) to the amount of CBD (or CBDA or an active analogue thereof) is of from about 100:1 to about 1:100. In some embodiments, the ratio of the amount of THC (or THCA or an active analogue thereof) to the amount of CBD (or CBDA or an active analogue thereof) is of from about 60:1 to about 1:60, from about 50:1 to about 1:50, from about 40:1 to about 1:40, from about 30:1 to about 1:30, from about 20:1 to about 1:20, from about 10:1 to about 1:10, from about 5:1 to about 1:5, from about 2:1 to about 1:2, from about 100:1 to about 1:10, from about 50:1 to about 1:20, from about 20:1 to about 1:50, from about 50:1 to about 1:10, or from about 25:1 to about 1:1.

In some embodiments, the ratio of the amount of THC (or THCA or an active analogue thereof) to the amount of CBD (or CBDA or an active analogue thereof) is of from about 100:1 to about 50:1, from about 80:1 to about 20:1, from about 70:1 to about 30:1, from about 60:1 to about 40:1, from about 50:1 to about 5:1, from about 40:1 to about 2:1, from about 30:1 to about 1:1, from about 20:1 to about 1:1, or from about 10:1 to about 1:1. In some embodiments, the ratio of the amount of THC (or THCA or an active analogue thereof) to the amount of CBD (or CBDA or an active analogue thereof) is of from about 1:100 to about 1:50 from about 1:80 to about 1:20, from about 1:70 to about 1:30, from about 1:60 to about 1:40, from about 1:50 to about 1:5, from about 1:40 to about 1:2, from about 1:30 to about 1:1, from about 1:20 to about 1:1, or from about 1:10 to about 1:1.

In some preferred embodiments, the ratio of the amount of THC (or THCA or an active analogue thereof) to the amount of CBD (or CBDA or an active analogue thereof) is of from about 5:1, about 10:1, about 20:1, about 25:1, or about 30:1. In some preferred embodiments, the ratio of the amount of THC (or THCA or an active analogue thereof) to the amount of CBD (or CBDA or an active analogue thereof) is of about 20:1. In some embodiments, the ratio of the amount of THC (or THCA or an active analogue thereof) to the amount of CBD (or CBDA or an active analogue thereof) is 20:1. In some embodiments, the cannabis butter formulation and/or the $CO_2$ extract cannabis oil formulation described herein specifically exclude THC. In some embodiments, the cannabis butter formulation and/or the $CO_2$ extract cannabis oil formulation described herein specifically exclude CBD. In some embodiments, the cannabis butter formulation and/or the $CO_2$ extract cannabis oil formulation described herein specifically exclude cannabinoids (i.e., no cannabinoid is present).

In some embodiments, the cannabis butter formulation or the $CO_2$ extract cannabis oil formulation is administered to the subject in multiple dosages for a treatment period of about 1 day to the remaining lifetime of the subject. In some embodiments, the cannabis butter formulation or the $CO_2$ extract cannabis oil formulation is administered to the subject in multiple dosages for a treatment period of about 1 week to about 52 weeks. In some embodiments, the cannabis butter formulation or the $CO_2$ extract cannabis oil formulation is administered to the subject for at least 2, at least 3, at least 4, at least 5, or at least 10 consecutive dosages or any number dosage therebetween. In some embodiments, the cannabis butter formulation or the $CO_2$ extract cannabis oil formulation is administered to the subject for at least 10, at least 12, at least 14, at least 16, or at least 20 consecutive dosages or any number dosage therebetween. In some embodiments, the cannabis butter formulation and the $CO_2$ extract cannabis oil formulation are administered to the subject in cycles, wherein each cycle comprises administering the cannabis butter formulation in 2, 3, 4, or 5 consecutive dosages, followed by administering of the $CO_2$ extract cannabis oil formulation in 2, 3, 4, or 5 consecutive dosages. In some embodiments, the cannabis butter formulation and/or the $CO_2$ extract cannabis oil formulation is administered in multiple dosages provided every 4-6 hours. In some embodiments, the cannabis butter formulation and/or the $CO_2$ extract cannabis oil formulation is administered in multiple dosages, seven times per week, for a treatment period of about 1 week to the remaining lifetime of the subject. In some embodiments, the cannabis butter formulation and/or the $CO_2$ extract cannabis oil formulation is administered in multiple dosages, wherein each dosage includes from about 5 mg to about 200 mg of tetrahydrocannabinol (THC), or tetrahydrocannabinolic acid (THCA), or an active analogue thereof. In some preferred embodiments, the ratio of the amount of THC (or THCA or an active analogue thereof) to the amount of CBD (or CBDA or an active analogue thereof) is of from about 5:1, about 10:1, about 20:1, about 25:1, or about 30:1. In some preferred embodiments, the ratio of the amount of THC (or THCA or an active analogue thereof) to the amount of CBD (or CBDA or an active analogue thereof) is of about 20:1. In some preferred embodiments, the ratio of the amount of THC (or THCA or an active analogue thereof) to the amount of CBD (or CBDA or an active analogue thereof) is approximately 20:1.

Dosage regimens can be adjusted to provide the optimal desired effect. For example, as discussed above, a single dose can be administered, several divided doses can be administered over time or the dose can be proportionally reduced or increased as indicated by the exigencies of the therapeutic situation. It is especially advantageous to formulate oral formulations in dosage unit form for ease of administration and uniformity of dosage. Dosage unit form, as used herein, refers to physically discrete units suited as unitary dosages for the human subjects to be treated; each unit containing a predetermined quantity of active compound calculated to produce the desired therapeutic effect in association with the required pharmaceutical carrier. Generally, the specification for the dosage unit forms are dictated by and directly dependent on (a) the unique characteristics of the therapeutic agent and the particular therapeutic or prophylactic effect to be achieved, and (b) the limitations inherent in the art of compounding such an active agent for the mitigation of tolerance in patients.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient can also be determined, as can the temporal requirements for administering each agent to provide a detectable therapeutic benefit to the patient. Accordingly, while certain dose and administration regimens are exemplified herein, these examples in no way limit the dose and administration regimen that can be provided to a patient in practicing the present disclosure.

It is to be noted that dosage values may vary with the type and severity of the condition to be mitigated, and may include single or multiple doses. It is to be further understood that for any particular subject, specific dosage regimens should be adjusted over time according to the individual need and the professional judgment of the person administering or supervising the administration of the formulations, and that dosage ranges set forth herein are exemplary only and are not intended to limit the scope or practice of the claimed composition. For example, doses can be adjusted based on pharmacokinetic or pharmacodynamic parameters, which may include clinical effects such as toxic effects and/or laboratory values. Thus, the present disclosure encompasses intra-patient dose-escalation as determined by the skilled artisan. Determining appropriate dosages and regimens for administration of therapeutic agents are well-known in the relevant art and would be understood to be encompassed by the skilled artisan once provided the teachings disclosed herein.

In some further embodiments, the methods relate to mitigating a tolerance effect from ingestion of cannabis-based formulations in a subject, wherein the subject has been pre-selected as having an increased risk of unresponsiveness to one or more antidepressants. In some embodiments, the methods relate to mitigating a tolerance effect from ingestion of cannabis-based formulations in a subject, wherein the subject has been previously treated with one or more antidepressant, and has developed at least a partial tolerance to the one or more antidepressant. As used herein, the term "antidepressant" or "antidepressant agent" refers to any compounds capable of alleviating the symptoms of depression. Further information regarding antidepressant agents can be found in, for example, the 1998 SIGMA catalogue and the "The Merck Index", 12th Ed., Budavari et al., eds., Merck & Co., Inc., Rahway, N.J., 1996. In some embodiments of this aspect and other aspects, at least one of the one or more antidepressant is a selective serotonin reuptake inhibitor (SSRI) pharmaceutical. Non-limiting examples of suitable SSRI pharmaceuticals include fluoxetine, fluoxetine hydrochloride, fluvoxamine, fluvoxamine maleate, citalopram, cericlamine, dapoxetine, escitalopram, femoxetine, indalpine, paroxetine, paxil, pexeva, sertraline, serzone, paroxetine, trazodone, trazodone hydrochloride, ifoxetine, cyanodothiepin, zimelidine, litoxetine; therapeutically active isomers or metabolites of any of the foregoing; and pharmaceutically acceptable salts, solvates, clathrates, polymorphs, or co-crystals of any one of the foregoing. In some embodiments, the one or more SSRI pharmaceuticals is selected from Prozac®, Zoloft®, Luvox, Luvox CR®, Faverin, Fevarin, Floxyfral, Dumyrox, Dividose®, Desyrel (trazodone HCl), and Paxil® (paroxetine hydrochloride).

Accordingly, in some embodiments of the methods disclosed herein, the subject has been pre-selected as having an increased risk of unresponsiveness to sertraline. In some embodiments, the subject has been pre-selected as having an increased risk of unresponsiveness to Zoloft® (sertraline HCl). In some embodiments, the subject has been previously treated with sertraline and has developed at least a partial tolerance to sertraline. In some embodiments, the subject has been previously treated with Zoloft® and has developed at least a partial tolerance to Zoloft®.

In some embodiments, the cannabis butter formulation and/or the $CO_2$ extract cannabis oil formulation as described herein is administered to the subject as a single therapeutic agent or in combination with one or more additional therapeutic agents or treatments. The term "administering in combination," as used herein with respect to the formulations described herein with another additional therapeutic agent or treatment, refers to co-administration or concurrent administration of a formulation described herein with another additional therapeutic agent or treatment, such that both can simultaneously and/or synergistically achieve a desired therapeutic effect. The two agents, however, need not be administered together. In some embodiments, administration of one agent can precede administration of the other. Simultaneous physiological effect need not necessarily require presence of both agents in the circulation at the same time.

In some embodiments, at least one of the one or more additional therapeutic agents is an antianxiety drug. As used herein, the term "antianxiety drug" refers to drugs used to treat anxiety. Suitable antianxiety drugs include, but are not limited to, agomelatine, alprazolam, aprepitant, bentazepam, buspirone, chlordiazepoxide, citalopram, clobazam, clonazepam, clorazepate, clotiazepam, delorazepam, dexmedetomidine, dextofisopam, diazepam, duloxetine, eglumegad, emapunil, eplivanserin, escitalopram, ethyl loflazepate, etifoxine, etizolam, fluoxetine, flurazepam, flutazolam, flutoprazepam, fluvoxamine, gabapentin, gepirone, halazepam, ipsapirone, itriglumide, ketazolam, levetiracetam, lorazepam, metaclazepam, mexazolam, moclobemide, nefazodone, ocinaplon, olanzapine, opipramol, oxazepam, oxazolam, pagoclone, paroxetine, pinazepam, pivagabine, prazepam, pregabalin, rilmazafone, S-desmethylzopiclone, sertraline, sumatriptan, tandospirone, tiagabine, tianeptine, tofisopam, venlafaxine, vestipitant, and zotepine; therapeutically active isomers or metabolites of any of the foregoing; and pharmaceutically acceptable salts, solvates, clathrates, polymorphs, or co-crystals of any one of the foregoing.

In some embodiments, at least one of the one or more additional therapeutic agents is an antidepressant. An antidepressant suitable for the methods describe herein can generally be any antidepressant and can be, for example, a selective serotonin reuptake inhibitor (SSRI), a selective norepinephrine reuptake inhibitors (SNRI), a tricyclic antidepressants (TCA), a monoamine oxidase inhibitors (MAOI), an atypical antidepressants, or a combination of any thereof. Accordingly, in some embodiments, the one or more additional therapeutic agents is selected from selective serotonin reuptake inhibitors (SSRIs), selective norepinephrine reuptake inhibitors (SNRIs), tricyclic antidepressants (TCAs), monoamine oxidase inhibitors (MAOIs), atypical antidepressants, and combinations of any thereof.

Selective serotonin reuptake inhibitors (SSRIs) are a class of pharmaceuticals typically used as antidepressants in the treatment of depression, anxiety disorders, and some personality disorder. Other well-known disorders that can be treated with SSRI's include dysthymia, premenstrual dysphoric disorder, panic disorder, obsessive compulsive disorder, social phobia, post-traumatic stress disorder, generalized anxiety disorder, obesity and alcoholism. Evidence is accumulating that such pharmaceuticals have also beneficial effects in less common disorders, such as trichotillomania, paraphilia and related disorders and borderline personality disorder. It has been reported that benefits are also obtained with use of an SSRI in smoking cessation and in the control of addictive behavior. In many individuals, it is not uncommon that SSRI treatments fail to have clear therapeutic results or have to be discontinued due to poor tolerance of side effects. For example, approximately one-third of patients with major depressive disorder fail to respond to a correctly delivered antidepressant treatment and only 20-30% of patients achieve remission.

Accordingly, in some embodiments, the cannabis butter formulation and/or the $CO_2$ extract cannabis oil formulation as described herein is administered to the subject in combination with one or more SSRIs. In some embodiments, the cannabis butter formulation and/or the $CO_2$ extract cannabis oil formulation as described herein is administered to the subject in combination with one, two, three, four, five, or six SSRIs. Exemplifications of suitable SSRI pharmaceuticals include, but are not limited to, fluoxetine, fluoxetine hydrochloride, fluvoxamine, fluvoxamine maleate, citalopram, cericlamine, dapoxetine, escitalopram, femoxetine, indalpine, paroxetine, paxil, pexeva, sertraline, serzone, paroxetine, trazodone, trazodone hydrochloride, ifoxetine, cyanodothiepin, zimelidine, litoxetine; therapeutically active isomers or metabolites of any of the foregoing; and pharmaceutically acceptable salts, solvates, clathrates, polymorphs, or co-crystals of any one of the foregoing. In some preferred embodiments, the one or more SSRI pharmaceuticals is selected from Prozac®, Zoloft®, Luvox, Luvox CR®, Faverin, Fevarin, Floxyfral, Dumyrox, Dividose®, Desyrel (trazodone HCl), and Paxil® (paroxetine hydrochloride). In some embodiments, at least one of the one or more SSRI pharmaceuticals comprises sertraline. In some embodiments, at least one of the one or more SSRI pharmaceuticals comprises Zoloft®.

Selective norepinephrine reuptake inhibitors (SNRIs) have been documented to block or delay the reuptake of the neurotransmitters, serotonin and norepinephrine, by the presynaptic nerves. This increases the levels of these two neurotransmitters in the synapse and tends to elevate mood.

Suitable SNRIs include, but are not limited to, venlafaxine (e.g., Effexor and Effexor CR), desvenlafaxine (e.g., Pristiq and Khedezla), milnacipran (e.g., Savella), duloxetine (e.g., Cymbalta), and levomilnacipran (e.g., Fetzima). Accordingly, in some embodiments, the cannabis butter formulation and/or the $CO_2$ extract cannabis oil formulation as described herein is administered to the subject in combination with one or more SNRIs. In some embodiments, the cannabis butter formulation and/or the $CO_2$ extract cannabis oil formulation as described herein is administered to the subject in combination with one, two, three, four, five, or six SNRIs.

Tricyclic antidepressants TCAs have been reported to increase levels of norepinephrine and serotonin, two neurotransmitters, and block the action of acetylcholine, another neurotransmitter. Non-limiting examples of TCAs suitable for the methods of the present disclosure include amitriptyline (e.g., Elavil), clomipramine (e.g., Anafranil), doxepin (e.g., Sinequan), imipramine (e.g., Tofranil), trimipramine (e.g., Surmontil), amoxapine (e.g., Amoxapine Tablets), desipramine (e.g., Norpramin), nortriptyline (e.g., Pamelor, Aventyl), and protriptyline (e.g., Vivactil). Accordingly, in some embodiments, the cannabis butter formulation and/or the $CO_2$ extract cannabis oil formulation as described herein is administered to the subject in combination with one or more TCAs. In some embodiments, the cannabis butter formulation and/or the $CO_2$ extract cannabis oil formulation as described herein is administered to the subject in combination with one, two, three, four, five, or six TCAs.

Monoamine oxidase inhibitors (MAOIs) have been reported to block the activity of monoamine oxidase, an enzyme that breaks down norepinephrine, serotonin, and dopamine in the brain and other parts of the body. Non-limiting examples of MAOIs suitable for the methods of the present disclosure include phenelzine (e.g., Nardil), selegiline (e.g., Emsam), and tranylcypromine (e.g., Parnate). Accordingly, in some embodiments, the cannabis butter formulation and/or the $CO_2$ extract cannabis oil formulation as described herein is administered to the subject in combination with one or more MAOIs. in some embodiments of the method disclosed herein, the cannabis butter formulation and/or the $CO_2$ extract cannabis oil formulation as described herein is administered to the subject in combination with one, two, three, four, five, or six MAOIs.

In some embodiments, the cannabis butter formulation and/or the $CO_2$ extract cannabis oil formulation as described herein is administered to the subject in combination with one or more atypical antidepressants. Atypical antidepressants are considered "atypical" because these therapeutic agents do not fit into any of the other classes of antidepressants. Each agent in this category has a unique mechanism of action in the body. However, like other antidepressants, atypical antidepressants affect the levels of dopamine, serotonin, and norepinephrine in the brain. For example, Brintellix and Viibryd inhibit reuptake of serotonin but also act on serotonin receptors. Suitable atypical antidepressant include, but are not limited to, bupropion (e.g., Wellbutrin), mirtazapine (e.g., Remeron), nefazodone (e.g., Serzone), trazodone (e.g., Desyrel and Oleptro), vilazodone (e.g., Viibryd), and vortioxetine (e.g., Brintellix). Accordingly, in some embodiments, the cannabis butter formulation and/or the $CO_2$ extract cannabis oil formulation as described herein is administered to the subject in combination with one, two, three, four, five, or six atypical antidepressants.

Diagnostic and Statistical Manual of Mental Disorders (DSM)

The DSM is the manual used by clinicians and researchers to diagnose and classify mental disorders, such as ADHD and ASD. The American Psychiatric Association (APA) published DSM-5 in 2013, culminating a 14-year revision process. APA is a national medical specialty society whose more than 36,000 physician members specialize in the diagnosis, treatment, prevention and research of mental illnesses.

Attention-deficit/Hyperactivity Disorder (ADHD)

The National Institute of Mental Health characterizes ADHD as one of the most common childhood disorders and it can continue through adolescence and adulthood. Most common symptoms include difficulty staying focused and paying attention, difficulty controlling behavior, and hyperactivity (over-activity).

Diagnostic Criteria for ADHD in the DSM-5

The two most significant changes to the DSM-5 with respect to ADHD are the recognition that individuals diagnosed with ADHD as children can continue to experience the disorder as an adult, and that individuals with ADHD may experience symptoms traditionally associated with ASD and vice-versa, such that a comorbid diagnosis is now permitted.

ADHD is generally characterized by a pattern of behavior that can result in performance issues in social, educational, or work settings. ADHD-related symptoms are generally divided into two categories (or types of deficits): 1) inattention, and 2) hyperactivity and impulsivity, that include behaviors like failure to pay close attention to details, difficulty organizing tasks and activities, excessive talking, fidgeting, or an inability to remain seated in appropriate situations. In order to be diagnosed with ADHD, children must have at least six symptoms from either (or both) the inattention group of criteria and the hyperactivity and impulsivity criteria, while older adolescents and adults (over age 17 years) must present with five:

Non-limiting Examples of Inattention Deficits for ADHD:

Often fails to give close attention to details or makes careless mistakes in schoolwork, at work, or with other activities.

Often has trouble holding attention on tasks or play activities.

Often does not seem to listen when spoken to directly.

Often does not follow through on instructions and fails to finish schoolwork, chores, or duties in the workplace (e.g., loses focus, side-tracked).

Often has trouble organizing tasks and activities.

Often avoids, dislikes, or is reluctant to do tasks that require mental effort over a long period of time (such as schoolwork or homework).

Often loses things necessary for tasks and activities (e.g. school materials, pencils, books, tools, wallets, keys, paperwork, eyeglasses, mobile telephones).

Is often easily distracted

Is often forgetful in daily activities.

Non-limiting Examples of Hyperactivity and Impulsivity Deficits for ADHD:

Often fidgets with or taps hands or feet, or squirms in seat.

Often leaves seat in situations when remaining seated is expected.

Often runs about or climbs in situations where it is not appropriate (adolescents or adults may be limited to feeling restless).

Often unable to play or take part in leisure activities quietly.

Is often "on the go" acting as if "driven by a motor".

Often talks excessively.

Often blurts out an answer before a question has been completed.

Often has trouble waiting his/her turn.

Often interrupts or intrudes on others (e.g., butts into conversations or games).

Because varying degrees of the above symptoms are common, to prevent over-diagnosis the following criteria must also be met:

Several inattentive or hyperactive-impulsive symptoms can be present before age 12 years.

Several symptoms are present in two or more setting, (e.g., at home, school or work; with friends or relatives; in other activities).

There is clear evidence that the symptoms interfere with, or reduce the quality of, social, school, or work functioning.

The symptoms do not happen only during the course of schizophrenia or another psychotic disorder. The symptoms are not better explained by another mental disorder (e.g. Mood Disorder, Anxiety Disorder, Dissociative Disorder, or a Personality Disorder).

While these criteria have not changed from DSM-4, examples have been included to illustrate the types of behavior children, older adolescents, and adults with ADHD might exhibit. The descriptions will help clinicians better identify typical ADHD symptoms at each stage of patients' lives. Using DSM-5, several of the individual's ADHD symptoms must be present prior to age 12 years, compared to 7 years as the age of onset in DSM-4. This change is supported by substantial research published since 1994 that found no clinical differences between children identified by 7 years versus later in terms of course, severity, outcome, or treatment response.

The Prevalence of ADHD

The Center for Disease Control and Prevention estimates that up to 11% of children and 4-5% of adults suffer from ADHD. Estimates of ADHD' s historic prevalence vary widely, at least in part because criteria for diagnosing the condition have evolved over time. Since 1997, there has been an upward national trend in parent-reported ADHD diagnoses, but it is not clear whether this trend is a result of an increase in the number of people who are actually suffering from ADHD or simply an increase in the number of diagnoses.

Autism Spectrum Disorder

The National Institute of Mental Health characterizes autism spectrum disorder (ASD) in the following manner: persistent deficits in social communication and social interaction across multiple contexts; restricted, repetitive patterns of behavior, interests, or activities; symptoms must be present in the early developmental period (typically recognized in the first two years of life); and, symptoms cause clinically significant impairment in social, occupational, or other important areas of current functioning.

The term "spectrum", as used herein, refers to the wide range of symptoms, skills, and levels of impairment or disability that individuals with ASD can have. Some individuals are mildly impaired by their symptoms, while others are severely disabled.

Diagnostic Criteria for ASD

Under the DSM-4, patients could be diagnosed with four separate autism-related disorders: autistic disorder, Asperger' s disorder, childhood disintegrative disorder, or the catch-all diagnosis of pervasive developmental disorder (PDD) not otherwise specified. Scientific studies found that these separate diagnoses were previously not consistently applied across different clinics and treatment centers. The DSM-5 now treats autism as a single umbrella disorder, without limiting the sensitivity of the criteria, or substantially changing the number of children being diagnosed.

Under the DSM-5 criteria, individuals with ASD must show symptoms from early childhood, even if those symptoms are not recognized until later. This criteria change is designed to encourage earlier diagnosis of ASD but also allows people whose symptoms may not be fully recognized until social demands exceed their capacity to receive the diagnosis. It is an important change from DSM-4 criteria, which was geared toward identifying school-aged children with autism-related disorders, but not as useful in diagnosing younger children.

Effective as of May 2013, licensed health care professionals, such as psychologists and psychiatrists, use the following diagnostic criteria when evaluating individuals for ASD:

A. Persistent deficits in social communication and social interaction across multiple contexts, as manifested by the following, currently or by history (examples are illustrative, not exhaustive):

1. Deficits in social-emotional reciprocity, ranging, for example, from abnormal social approach and failure of normal back-and-forth conversation; to reduced sharing of interests, emotions, or affect; to failure to initiate or respond to social interactions.

2. Deficits in nonverbal communicative behaviors used for social interaction, ranging, for example, from poorly integrated verbal and nonverbal communication; to abnormalities in eye contact and body language or deficits in understanding and use of gestures; to a total lack of facial expressions and nonverbal communication.

3. Deficits in developing, maintaining, and understanding relationships, ranging, for example, from difficulties adjusting behavior to suit various social contexts; to difficulties in sharing imaginative play or in making friends; to absence of interest in peers.

B. Restricted, repetitive patterns of behavior, interests, or activities (collectively called "deficits"), as manifested by at least two of the following, currently or by history (examples are illustrative, not exhaustive):

1. Stereotyped or repetitive motor movements, use of objects, or speech (e.g., simple motor stereotypes, lining up toys or flipping objects, echolalia, idiosyncratic phrases).

2. Insistence on sameness, inflexible adherence to routines, or ritualized patterns or verbal nonverbal behavior (e.g., extreme distress at small changes, difficulties with transitions, rigid thinking patterns, greeting rituals, need to take same route or eat same food every day).

3. Highly restricted, fixated interests that are abnormal in intensity or focus (e.g., strong attachment to or preoccupation with unusual objects, excessively circumscribed or perseverative interest).

4. Hyper- or hypo-reactivity to sensory input or unusual interests in sensory aspects of the environment (e.g., apparent indifference to pain/temperature, adverse response to specific sounds or textures, excessive smelling or touching of objects, visual fascination with lights or movement).

C. Symptoms must be present in the early developmental period (but may not become fully manifest until social demands exceed limited capacities, or may be masked by learned strategies in later life).

D. Symptoms cause clinically significant impairment in social, occupational, or other important areas of current functioning.

E. These disturbances are not better explained by intellectual disability (intellectual developmental disorder) or global developmental delay. Intellectual disability and autism spectrum disorder frequently co-occur; to make comorbid diagnoses of autism spectrum disorder and intellectual disability, social communication should be below that expected for general developmental level.

The Prevalence of Autism Spectrum Disorder

As with ADHD, ASD diagnoses have been increasing over the past several decades. Estimates vary, but during the 1970s and 1980s, approximately 1 in every 2,000 children was believed to have autism. According to the Center for Disease Control and Prevention, in the year 2000 it was believed that approximately 1 in 150 children (or 6.7 children per 1,000) were identified as having an autism spectrum disorder. In 2010, the number was believed to be as high as 1 in 68 (or 14.7 children in 1000). There is ongoing debate about whether the prevalence of autism is truly increasing or whether the most recent estimates of its prevalence simply reflect a growing awareness of the condition and/or an expanded definition of what constitutes autism.

Overlapping Deficits in Patients Suffering from ADHD and ASD

According to Leitner, Y., Frontiers in Human Neuroscience (2014) Vol. 8, Article 268, pages 1-8 (hereinafter "Leitner (2014)"), "[i]n the last decade, studies have reported increased prevalence of both attention deficit hyperactivity disorder (ADHD) and autism spectrum disorders (ASD). While they are still considered distinct conditions with distinct diagnostic criteria, studies show that between 30 and 50% of individuals with ASD manifest ADHD symptoms (particularly at pre-school age), and similarly, estimates suggest two-thirds of individuals with ADHD show features of ASD."

Further, "[b]oth disorders have a known genetic pre-disposition, with comorbidity within the same individual and across family members . . . [and] [e]vidence for common neurobiological substrates has been found through similarities in neuropsychological profiles in individuals with both disorders."

As exemplified by Leitner (2014), there is a growing consensus within the scientific community that ADHD and ASD share similar symptom profiles and involve certain of the same core cognitive and behavioral deficits. See also Susan Dickerson Mayes and Susan L. Calhoun, Research in Autism Spectrum Disorders, January-March 2012, Vol. 6(a): 277-285, Autism and ADHD: Overlapping and Discriminating Symptoms ("[t]he core symptoms of ADHD (attention deficit, impulsivity, and hyperactivity) are part of autism, and autism and ADHD have similar underlying neuropsychological deficits").

In addition, scientists believe that there are common genetic influences operating across autistic and ADHD traits and behaviors, and that ADHD and ASD share certain susceptibility genes. This is described in several scientific articles: Ronald, A., et al., Evidence and overlapping genetic influences on autistic and ADHD behaviors in a community twin sample, The Journal of Child Psychology and Psychiatry, May 2008, Vol. 49:5 pp. 535-42; and Rommelse, N., et al., Shared heritability of attention-deficit/hyperactivity disorder and autism spectrum disorder, European Child & Adolescent Psychiatry, March 2010, Vol. 19:3, pp. 281-295.

Listed below are several, but not all, deficits associated with both ASD and ADHD that are effectively treated with THC. This list is not intended to be exhaustive.

1. Deficits in hyperactivity, impulsivity and inattention, including any associated cognitive, behavioral and motor impairments arising therefrom. See DSM 5. See also Susan Dickerson Mayes and Susan L. Calhoun, Research in Autism Spectrum Disorders, January-March 2012, Vol. 6(a): 277-285, Autism and ADHD: Overlapping and Discriminating Symptoms ("[t]he core symptoms of ADHD (attention deficit, impulsivity, and hyperactivity) are part of autism, and autism and ADHD have similar underlying neuropsychological deficits").

2. Timing Deficits

A recent survey of the scientific literature relating to timing abnormalities in ADHD patients concludes that, "ADHD patients are consistently impaired in three major timing domains, in motor timing, perceptual timing and temporal foresight." (See Noreika V., et al. (2013) Jan. 51(2):235-66, Neuropsychologia, Timing deficits in attention-deficit/hyperactivity disorder (ADHD): evidence from neurocognitive and neuroimaging studies (hereinafter "Noreika").) As stated in Noreika, for individuals with ADHD, "an interval may seem to contain more seconds than it actually has . . . suggesting that internal time runs faster for them than it does for typically developing individuals."

Consistent with this observation, time estimation deficits observed in ADHD children include the over-estimation and under(re)production of time intervals as compared to others, consistent with a relatively fast internal sense of time. (See Rubia, K., et al., Impulsiveness as a timing disturbance: neurocognitive abnormalities in attention-deficit hyperactivity disorder during temporal processes and normalization with methylphenidate, Phil. Trans. R. Soc. B (2009) 364, 1919-1931 (hereinafter "Rubia 2009"); Rubia, K. et al., Performance of children with attention deficit hyperactivity disorder (ADHD) on a test battery of impulsiveness, Child Neuropsychol. (2007) 13, 276-304; and Toplak, M. E., et al., Temporal information processing in ADHD: findings to date and new methods, J. Neurosci. Methods (2006) 151, 15-29.) In Rubia 2009, the authors conclude that, "[t]his review together with the new empirical findings demonstrates that neurocognitive dysfunctions in temporal processes are crucial to the impulsiveness disorder of ADHD." Notably, ADHD children are also prone to make consistently premature responses across discrete tasks, suggesting the presence of an underlying timing disturbance that is not task specific. (See Rubia et al., Synchronization, anticipation and consistency of motor timing in dimensionally defined children with attention deficit hyperactivity disorder, Perceptual and Motor Skills (1999) 89, 1237-1258; Ben-Pazi, H. et al., Abnormal rhythmic motor response in children with attention-deficit-hyperactivity disorder, Developmental Medicine and Child Neurology (2003) 45, 743-45 (hereinafter "Ben-Pazi 2003"); and Ben-Pazi, H. et al., Age and medication effects on rhythmic responses in ADHD: Possible oscillatory mechanisms, Neuropshychologia (2006); 44, 412-416 (hereinafter "Ben-Pazi 2006").)

Studies of timing deficits among autistics are relatively new and limited in number, but most of the available evidence, along with clinical and familial observations, suggests that ASD, like ADHD, is associated with a timing disturbance. (See Allman, M., et al., Developmental neuroscience of time and number: implications for autism and other neurodevelopmental disabilities, Front. Integr. Neurosci (2012) 6:7.) Falter, C. and Valdas, N., Interval Timing Deficits and Abnormal Cognitive Development, Front. Integr. Neurosci. (2011) 5:26, describe how, "[a] secondary symptom observed in both ASD and ADHD is abnormal interval timing, i.e., processing of stimulus duration."

In the book entitled, "Sensory Perceptual Issues in Autism and Asperger Syndrome, Different Sensory Experiences Different Perceptual Worlds", Bogdashina, O., pp. 77-78, it is explained how, "[autistics] subjective experience of time is also different from that of non-autistics. For them, time might seem faster, whereas non-autistic people may think that autistic children are slow in their decision-making."

Furthermore, Martin, J. S., et al., Brief report, Impaired temporal reproduction performance in adults with autism spectrum disorder, J. Autism Dev. Disord (2010) May 40(5); 640-6, describes how, an "ASD group was less successful at time reproductions than [the] comparison group and were more variable in their responses." In addition, Szelag, E., et al., Temporal processing deficits in high-functioning children with autism, British Journal of Psychology; 2004 Aug, 95:3 pp. 269-282, discuss how, "important deficits in duration judgment [occur] in individuals with autism."

3. Deficits in Social Interaction

Deficits in social interaction include, but are not limited to, an individual's ability to interpret body language, read non-verbal cues, and in the ability to form and maintain interpersonal relationships. This deficit is described in DSM-5 and in Leitner (2014). In addition, Barkley, R. A., et al. (1990) Comprehensive evaluation of attention deficit disorder with and without hyperactivity as defined by research criteria, J. Consult. Clin. Psychol. 58, 775-789, describes how inattentiveness among ADHD children may cause "miss[ed] social cues." Marton, I., et al. (2009) Empathy and social perspective taking in children with attention-deficit/hyperactivity disorder, J. Abnorm. Child Psychol. 37, 107-118, discusses how children with ADHD use lower levels of social perspective taking in their definition of problems, identification of feelings, and evaluation of outcomes. Social-communication deficits are also common in individuals suffering from ASD, where some patients exhibit a near complete inability to understand basic social conventions. (See Leitner (2014) and DSM-5).

4. Deficits in Controlling Repetitive Behaviors

Repetitive behaviors are common in individuals with ASD and can include stereotyped behaviors, interests and activities, inflexibly adhering to routines and rituals, and repetitive movements, as discussed in Militerni, R., et al., Repetitive behaviors in autistic disorder, European Child & Adolescent Psychiatry, 11:210-218 (2002). Similarly, ADHD is often comorbid with obsessive-compulsive disorders, as described in Sheppard, B., et al., ADHD prevalence and association with hoarding behaviors in childhood-onset OCD, Depression and Anxiety, Volume 27, Issue 7, pp. 667-674, and Masi, G., et al., Comprehensive Psychiatry 2006, Vol. 47:1, Jan.-Feb. 2006, pp. 42-47.

5. Deficits in Oral Communication Skills

Individuals with ASD exhibit varying difficulties in the development of language skills, with some individuals lacking the ability to speak altogether. A majority of autistics have difficulty orally communicating with others and can exhibit tendencies to simply repeat words or questions that were just heard or heard at an earlier time, a phenomenon described as "echolalia." (See U.S. Dept. of Health and Human Services, National Institutes of Health: Communication Problems in Children with Autism Spectrum Disorder (http://www.nidcd.nih.gov/health/voice/pages/communication-problems-in-children-with-autism-spectrum-disorder.aspx).) Similarly, individuals with ADHD, especially children, exhibit problems with oral communication skills, including: 1) excessive verbal output under certain conditions; 2) decreased verbal output and increased errors when giving directions or story telling; and 3) timing problems associated with initiating conversations, taking turns, and maintaining or changing topics during conversations (see Bruce, B., et al., ADHD and language impairment, Eur Child Adlesc. Psychiatry (2006) 15:52-60).

6. Deficits in Motor Skills

Individuals with ASD commonly exhibit impaired posture, balance, speed, and coordination. (See Noterdaeme, M., et al., Evaluation of neuromotor deficits in children with autism and children with a specific speech and language disorder, Eur. Child Adolesc. Psychiatry, 2002 Oct; 11(5): 219-25; and Rinehart, N.J., Gait function in newly diagnosed children with autism: Cerebellar and basal ganglia related motor disorder; Dev. Med. Child Neurol. 2006 Oct; 48(10); 819-24.). Similarly, individuals with ADHD tend to exhibit motor skill impairments as compared to individuals without ADHD, as described in Pitcher, T, et al., Fine and Gross Motor Ability in Males with ADHD, Developmental Medicine & Child Neurology, August (2003) Volume, Issue 08; and Tseng, M., et al, Relationship between motor proficiency, attention, impulse and activity in children with ADHD, Developmental Medicine & Child Neurology, Volume, Issue 06, June 2005 pp. 381-388.

7. Deficits in Visual/Spatial Problem Solving

People with ADHD perform significantly poorer than other individuals on certain visual spatial problems and tasks, as described in Semrud-Clikeman, M. (2012) The role of inattention on academics, fluid reasoning, and visual-spatial functioning in two subtypes of ADHD, Appl Neuropsychol Child, 1(1):18-29. Individuals suffering from ASD also show inhibited performance on certain visual-spatial tasks, as described in Kozcat, D. L., et al., (2002) Eye movement abnormality suggestive of a spatial memory deficit is present in parents of autistic probands, Journal of Child Psychology and Psychiatry 32(6) 513-518; and Steele, S.D. et al. (2007) Spatial Working Memory Deficits in Autism, Journal of Autism and Developmental Disorders 37 (4): 605-612.

8. Deficits in Sensory Processing

A deficit in sensory processing can be, for example, an atypical response to sensory stimuli. Atypical responses to sensory stimuli are frequently reported in individuals suffering from ASD and ADHD. This is described in Crane, L., et al., Sensory processing in adults with autism spectrum disorders, Autism, May (2009) 13: 215-228; and Miller, L., et al., Autism, May (2014) Vol. 18, no. 4:428-423 (hereinafter "Miller"). Miller states how, "[s]ensory over-responsivity correlated positively with autistic traits at a significant level across groups and within groups. Adults with autism spectrum conditions experience sensory over-responsivity to daily sensory stimuli to a high degree." In addition, Ghanizadeh, A., Sensory Processing Problems in Children with ADHD, a Systematic Review, Psychiatry Investig. (2011) Jun, 8(2):89-94, describes how "[s]ensory processing problems in children with ADHD are more common than in typically developing children."

THC is effective at reducing or eliminating these problematic symptoms and deficits common to both disorders, with fewer significant side effects than other medications, as shown in the Examples section below.

Tetrahydrocannabinol (THC)

As described above, Δ9-tetrahydrocannabinol (Δ9-THC or THC), also known by its International Non-Proprietary Name (INN) dronabinol, is the principal psychoactive constituent (or cannabinoid) of the *Cannabis* plant. The initially synthesized and accumulated form in plant is THC acid (THCA). An aromatic terpenoid, THC has a very low solubility in water, but good solubility in most organic solvents, specifically lipids and alcohols. In general, THC has mild to moderate analgesic effects, and cannabis can be used to treat pain by altering transmitter release on dorsal root ganglion of the spinal cord and in the periaqueductal gray. Other effects include relaxation, alteration of visual, auditory, and olfactory senses, fatigue, and appetite stimulation. THC has marked antiemetic properties, and may also reduce aggression in certain subjects. Recent evidence suggests that THC helps alleviate symptoms suffered both by AIDS patients, and by cancer patients undergoing chemotherapy, by increasing appetite and decreasing nausea. It has also been shown to assist some glaucoma patients by reducing pressure within the eye, and is used in the form of cannabis by a number of multiple sclerosis patients, who use it to alleviate neuropathic pain and spasticity. There are four stereoisomers of THC, but only the (−)-trans isomer occurs naturally (CAS-1972-08-03). The fully systematic name for this THC isomer is (−)-(6aR,10aR)-6,6,9-trimethyl-3-pentyl- 6a,7,8,10a-tetrahydro-6H-benzo[c]chromen-1 -ol. Two related substances, Δ9-tetrahydrocannabinol-2-oic acid and Δ9-tetrahydrocannabinol-4-oic acid (THCA), are also present in cannabis, sometimes in large amounts. During smoking, THCA is partly converted to THC. The active isomer Δ8-THC, in which the unsaturated bond in the cyclohexene ring is located between C-8 and C-9, is found in much smaller amounts.

An aromatic terpenoid, THC has a very low solubility in water, but good solubility in most organic solvents, specifically lipids and alcohols.

Other substances that occur in cannabis include cannabidiol (CBD) and, in aged samples, cannabinol (CBN), both of which have quite different pharmacological effects to THC. THC and about 80 other molecules make up the phytocannabinoid family.

The chemical formula of THC is $C_{21}H_{30}O_2$, with a molecular weight of 314.4 g/mol.

Molecular Structure (1)

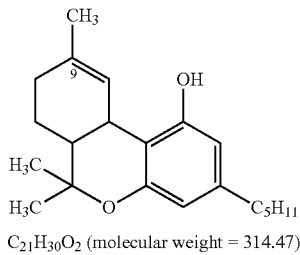

$C_{21}H_{30}O_2$ (molecular weight = 314.47)

(1) Δ9-tetrahydrocannabinol, the major psychoactive principle of *Cannabis*, showing the partial ring numbering system in the more common dibenzofuran system.

A composition comprising THC, as disclosed herein, can be a composition comprising tetrahydrocannabinol, an isomer of tetrahydrocannabinol, a stereoisomer of tetrahydrocannabinol, a trans isomer of tetrahydrocannabinol, a derivative of tetrahydrocannabinol, a metabolite of tetrahydrocannabinol (for example, 11-OH-THC, 11-COOH-THC, 11-OH-delta 9 THC, or 11-nor-delta-9-THC-9-carboxylic acid (11-nor-acid)), delta-9-THC, or a synthetic tetrahydrocannabinol. THC can be chemically synthesized or extracted from *Cannabis sativa* L. (marijuana).

THC can be an isomer of tetrahydrocannabinol, a stereoisomer of tetrahydrocannabinol, a trans isomer of tetrahydrocannabinol, a derivative of tetrahydrocannabinol, a metabolite of tetrahydrocannabinol (for example, 11-OH-THC, 11-COOH-THC, 11-OH-delta 9 THC, or 11-nor-delta-9-THC-9-carboxylic acid (11-nor-acid)), delta-9-THC, or a synthetic tetrahydrocannabinol. THC can be chemically synthesized or extracted from *Cannabis sativa* L. (marijuana).

A method for the isolation of delta-9-tetrahydrocannabinol (THC) from, cannabis plant material is described, for example, in U.S. Pat. No. 6,730,519. A method and apparatus for processing the plant cannabis is described, for example, in U.S. Pat. No. 4,279,824. A method for producing an extract from cannabis plant matter, containing a tetrahydrocannabinol and a cannabidiol is described in, for example, U.S. Pat. No. 8,895,078.

Dronabinol/Marinol®

Dronabinol is designated chemically as (6aR-trans)-6a,7,8,10a-tetrahydro-6,6,9-trimethyl-3-pentyl-6H-dibenzo[b,d]pyran-1-ol. Dronabinol, is available by prescription in the U.S. and Canada under the brand name Marinol®. Actativ, Inc. (USA) is one distributor of prescription dronabinol.

Dronabinol, the active ingredient in MARINOL® (dronabinol) Capsules, is synthetic delta-9-tetrahydrocannabinol (delta-9-THC). Delta-9-tetrahydrocannabinol is also a naturally occurring component of *Cannabis sativa* L. (marijuana).

MARINOL (dronabinol) Capsules are supplied as round, soft gelatin capsules containing 2.5 mg, 5 mg, or 10 mg dronabinol. Each MARINOL (dronabinol) Capsule strength is formulated with the following inactive ingredients: 2.5 mg capsule contains, gelatin, glycerin, sesame oil, and titanium dioxide; 5 mg capsule contains, iron oxide red and iron oxide black, gelatin, glycerin, sesame oil, and titanium dioxide; and 10 mg capsule contains, iron oxide red and iron oxide yellow, gelatin, glycerin, sesame oil, and titanium dioxide.

Pharmacology of THC and CBD

1. Mechanism of Action: Derivative of *Cannabis sativa*; contains tetrahydrocannabinol (THC), an analogue of endogenous neurotransmitter anandamide.

2. Absorption: bioavailability: 10-20%; peak plasma time: 0.5-4 hr.

3. Distribution: protein bound: 90-99%; Vd: 10 L/kg.

4. Metabolism: extensive first-pass hepatic metabolism; metabolites: 11-hydroxy-delta-9-tetrahydrocannabinol (active).

5. Elimination: half-life: parent drug, 25-36 hr; metabolites, 44-59 hr; renal clearance: 18-20 mL/min; total body clearance: 0.2 L/kg/hr; excretion: feces (50%), urine (15%).

The pharmacological actions of THC result from its partial agonist activity at the cannabinoid receptor CB1, located mainly in the central nervous system, and the CB2 receptor, mainly expressed in cells of the immune system. The psychoactive effects of THC are believed to be primarily mediated by its activation of CB1 G-protein coupled receptors, which result in a decrease in the concentration of the second messenger molecule cAMP through inhibition of adenylate cyclase. It is also suggested that THC has an anticholinesterase action which may implicate it as a potential treatment for Alzheimer's and Myasthenia.

Cannabidiol (CBD) is another important cannabinoid found in *Cannabis*. Cannabidiol has been shown to exhibit sedative effects in animal tests. Some research, however, indicates that CBD can increase alertness, and attenuate certain of the psychoactive effects of THC. In this regard, CBD may decrease the rate of THC clearance from the body, perhaps by interfering with the metabolism of THC in the liver. Medically, it has been shown to relieve convulsion, inflammation, anxiety, and nausea, as well as inhibit cancer cell growth. Recent studies have shown cannabidiol to be as effective as atypical antipsychotics in treating schizophrenia. Other studies have also shown that CBD may relieve symptoms of dystonia and reduces growth of aggressive human breast cancer cells in vitro and reduces their invasiveness.

Cannabidiol has been reported to decrease activity of the limbic system and to decrease social isolation induced by THC. It has also been reported that Cannabidiol reduces anxiety in social anxiety disorder. Cannabidiol has also been reported as being effective in treating an often drug-induced set of neurological movement disorders known as dystonia. In addition, it has been reported in some studies that strains of *Cannabis* which contained higher concentrations of Cannabidiol did not produce short-term memory impairment vs. strains which contained similar concentrations of THC. Pharmacologically speaking, cannabidiol acts as an indirect antagonist of cannabinoid agonists. CBD is an antagonist at the putative new cannabinoid receptor, GPR55. Cannabidiol has also been shown to act as a 5-HT1A receptor agonist, an action which is involved in its antidepressant, anxiolytic, and neuroprotective effects. Cannabidiol has also been reported to be an allosteric modulator at the Mu and Delta opioid receptor sites.

Problems with the Existing Scientific Literature Regarding the Effect of THC on Human Cognition.

1. The Conventional "Wisdom."

The impression created by most of the available scientific literature is that THC has a negative influence on human cognition and mental health. As described in Tsuang, M., et al., *Cannabis* use and cognitive dysfunction, Indian J. Psychiatry (2011) Jul-Sep.; 53(3), "[t]he general impression supported by many studies is that cannabis causes cognitive decline, particularly with long-term usage." The majority of older studies have suggested a significant cognitive decline in cannabis abusers compared to non-users. For example, Nava, F., et al., $0_2$ dopamine receptors enable $\Delta 9$-tetrahydrocannabinol induced memory impairment and reduction of hippocampal extracellular acetylcholine concentration, British Journal of Pharmacology (2000) 130, 1201-1210, states that although, "there is no question concerning the cognitive deficits present during marijuana intoxication, there is some doubt whether or not permanent memory deficits occur after chronic use." Nava then concludes that marijuana induces "difficulty with thinking and problem-solving" and "has also been linked to other mental health problems" such as depression and anxiety.

Some researchers, however, acknowledge that a causal link between marijuana use, cognitive deficits, and mental illness has not been credibly established and acknowledge that the co-occurrence of cognitive impairments, mental health issues and marijuana consumption could be the result of baseline cognitive impairments and/or self medicating to treat pre-existing conditions. (See Sofuoglu, M., et al., Cognitive Function as an Emerging Treatment for Marijuana Addiction, Exp. Clin. Psychopharmacol (2010) Apr, 18(2): 109-119.) (Emphasis added). Even the National Institutes of Health (NIH), notes that, "[t]he ability to draw definitive conclusions about marijuana's long-term impact on the human brain from past studies is often limited by the fact that study participants use multiple substances, and there is often limited data about the participants' health or mental functioning prior to the study." (Emphasis added).

2. In Reality, There is Limited Credible Research into THC's Effects on Human Cognition.

The American Medical Association changed its stance on marijuana in 2009, adopting a policy of promoting clinical research into the development of cannabis-based medicines. This change in policy was made in part due to the absence of an adequate amount of credible research into marijuana's effects on humans. Individual doctors and scientists are also calling for further research into the potential therapeutic effects of marijuana because approximately 94% of U.S. studies into marijuana were specifically designed to investigate the drug's potential harm, whereas only about 6% of past U.S. studies investigate potential benefits. http://www.cnn.com/2013/08/08/health/gupta-changed-mind-marijuana/.

3. Older Research Doesn't Meet Current Clinical Standards.

There are a number of problems with the existing research into marijuana's effects on human cognition, separate and apart from the obvious historical bias in favor of investigating harm. One major problem is that much of the older research, the research upon which marijuana's classification as a Schedule 1 controlled substance is based, does not meet current clinical standards. As Grant, I., et al., Non-acute (residual) neurocognitive effects of cannabis use: a meta-analytic study, J. Int. Neuropsychol Soc. (2003) Jul, 9(5): 679-89, points out, "few studies into the non-acute neurocognitive effects of cannabis meet current research standards."

4. Lack of Properly Designed Research Studies.

Yet another problem is that there has been little if any effort to determine whether THC (or marijuana for that matter) might operate to produce different effects in different populations by, for example, comparing the effects of THC on individuals suffering from ADHD with that of a control population. Or, comparing the effects of THC on individuals suffering from ASD with that of a control population.

5. Some of the Existing Research Doesn't Differentiate Between the Chemical Constituents of the *Cannabis* Plant.

Another problem with the existing research is that it in large part fails to isolate the effects of the various chemical constituents of the cannabis plant. There are different types of cannabinoids in the cannabis plant (of which THC is just one) and different types of cannabinoids are believed to have differing effects on the human body. One cannabinoid, cannabidiol (CBD), is believed to produce therapeutic effects that differ from the effects produced by THC and may actually operate to block or lessen the effects of THC in humans (see A. W. Zuardi et al., Action of Cannabidiol on the Anxiety and Other Effects Produced by Delta-9 THC in Normal Subjects). Accordingly, studies predicated on smoking the cannabis plant naturally fail to account for the varying quantities of these chemical components that may be present in the cannabis plant and the effect that these variations may have on human thought and behavior patterns.

6. Improper Inferences Have Been Drawn From the Existing, Flawed Research

One of the most serious problems with the existing research into marijuana's effects on human cognition is the improper conclusions that are drawn from it. In particular, some studies suggest a correlation between marijuana use, cognitive deficits (including lower IQ) and the presence of mental illness, although recent studies contradict these findings. Putting aside the dispute over the validity of the correlation, some have used the correlation to suggest causation; that is, that the cognitive deficits and mental illnesses that are sometimes found to occur among marijuana users are caused by marijuana use, rather than pre-existing. But it is equally likely that individuals with mental illnesses and cognitive deficits are self-medicating with marijuana and other drugs. As acknowledged by the NIH, absent a baseline assessment of cognitive performance and propensity for mental illness prior to inception of cannabis use, no conclusion about a causal relationship can be drawn.

Amresh, S., et al., *Cannabis* use and cognitive dysfunction, Indian J Psychiatry (2011) Jul-Sep, 53(3): 187-191, notes that, "[a]lthough the general impression supported by many studies is that cannabis causes cognitive decline, particularly with long-term usage, some research suggests that this may not be the case." Moreover, recent studies find no significant effects on cognitive performance in marijuana users, see Hart, C. L., et al., Effects of acute smoked marijuana on complex cognitive performance, Neuropsychopharmacology (2001) Nov, 25(5):757-65 (hereinafter "Hart"). Hart discusses how experienced THC users, when performing tasks under the influence of THC, showed no deficits in "accuracy on measures of cognitive flexibility, mental calculation and reasoning." Hart then concludes that, [t]hese data demonstrate that acute marijuana smoking produced minimal effects on complex cognitive task performance in experienced marijuana users," and that there was no relationship between marijuana use and mental or physical health problems. Pardini, D., et al., Chronic Adolescent Marijuana Use as a Risk Factor for Physical and Mental Health Problems in Young Adult Men, Psychology of Addictive Behaviors (2015) Vol. 29, No. 3, 552-563, describes how, "[a]fter controlling for potential confounding variables such as alcohol, tobacco, and hard drug use, socioeconomic status, whether the young men had health insurance, and early health status (prior to marijuana use), findings from this sample indicated that chronic marijuana users were not more likely than late increasing users, adolescence-limited users, or low/nonusers to experience several physical or mental health problems in their mid-30s. In fact, there were no significant differences between marijuana trajectory groups in terms of adult health outcomes, even when models were run without controlling for potential confounds."

Another problem with the existing research is that many experiments test chronic THC users, but the testing occurs when the subjects are not under the influence of THC. Researchers then conclude that prior THC caused a cognitive impairment or deficit, when the cognitive impairment (deficit) is equally likely to have been pre-existing.

As an example, one study evaluated the performance of former cannabis users on tasks that required the filtering of irrelevant information. The ex-cannabis users were not under the influence of cannabis during the testing. The study found an impaired ability to focus attention and filter irrelevant information and, as a result, concluded that cannabis use can have adverse effects on the ability to effectively reject irrelevant information. (See Solowij, N., Do cognitive impairments recover following cessation of cannabis use? Life Sci. 1995, 56(23-24):2119-26.) There is an obvious problem with this study. It is the implication that cannabis use caused the impairment in the ability to screen irrelevant information. The inference is improper because there is no baseline evaluation of how the subjects would have performed prior to cannabis use, to rule out the possibility that these individuals had baseline impairments in their ability to screen irrelevant information in the first place. Based on the results of the experiments disclosed in the Examples section, provided below, it is entirely possible that some or all of the cannabis users in this study used cannabis to improve focus and reduce their responsiveness to peripheral distractions. Other studies suffer from similar defects, namely the testing of cannabis users, who are not under the influence of cannabis during the test, without establishing a baseline measure of cognitive performance prior to cannabis use.

7. The Existing Scientific Literature Does not Appreciate That Oral Consumption is Required for Optimal Results.

A practical consideration is that many people consume THC in its least efficient form, smoking the flower. Smoking or vaporizing marijuana is less efficient than orally consuming THC for three reasons: 1) much of the active ingredient is wasted as un-inhaled smoke; 2) smoking results in the ingestion of substances in the marijuana plant that may counteract or alter the effects of THC in humans (e.g., CBD); and, perhaps most importantly, 3) smoking marijuana avoids the amplifying effects that occur when THC is processed through the liver. Specifically, when eaten, cannabis is metabolized by the liver, and delta-9 THC is converted to 11-hydroxy-THC, which passes the blood-brain barrier more rapidly, and produces stronger and longer lasting effects than smoking.

Not only is oral consumption required for optimal results, but also an accurate dosage of THC is required for optimal results. Smoking or vaporizing marijuana is less effective because it is difficult to determine the dosage of the active ingredient THC that is being inhaled, combustion of the plant involves ingestion of other substances that affect the efficacy of the active ingredient, and the effects are shorter-lasting. As shown in the Examples section below, consumption of THC through oral administration produces significantly stronger therapeutic effects than vaporizing on many of the symptoms and deficits exhibited by individuals suffering from ADHD and ASD. Administered THC to treat ADHD or ASD.

THC is an effective treatment for ADHD and ASD. It is also an effective treatment for one or more of the symptoms or deficits commonly associated with ADHD or ASD, and for certain commonly occurring comorbid conditions. The methods of the present disclosure are effective in the treatment of patients who are children, adolescents or adults and there is not a significant difference in the symptoms or the details of the manner of treatment among patients of different ages.

Oral administration of THC is an effective treatment for ADHD and ASD. It is also an effective treatment for one or more of the symptoms or deficits commonly associated with ADHD or ASD, and for certain commonly occurring comorbid conditions. The methods of the present disclosure are effective in the treatment of patients who are children, adolescents or adults and there is not a significant difference in the symptoms or the details of the manner of treatment among patients of different ages.

THC is believed to affect human cognition and behavior by mimicking the naturally-occurring neurotransmitter anandamide. Anandamide was first isolated and described in 1992 by a team of researchers at the Hebrew University of Jerusalem. Anandamide binds to parts of the brain known as endocannibinoid receptors, so named because scientists discovered that THC, a cannabinoid, interacts with these parts of the brain before THC's naturally-occurring counterpart, anandamide, was discovered. The endocannibinoid receptors are located in regions of the brain that affect emotions, motivation, coordination, balance, learning and memory, and timing, among other functions. Little is currently known about anandamide's specific role in regulating human behavior, but it is believed to be involved in the regulation of cognition, movement, motivation, and pleasure. The Examples section below, shows that natural and synthetic substitutes for anandamide, like THC, are effective treatments for regulating symptoms commonly associated with ASD and ADHD. THC, for example, reduces anxiety, resolves timing deficits (by slowing perception of time), reduces inattention and hyperactivity (while increasing focus and attention), reduces obsessive-compulsive tendencies, and/or improves the mood of individuals with ADHD or ASD.

Diagnosing of ADHD or ASD

ADHD symptoms are relatively common, and most people have been in contact with children, if not adults, who exhibit some or all of the symptoms of the disorder. A diagnosis of ADHD or ASD can be made by a licensed health care profession, for example, a clinician, a medical doctor, a physician, a psychiatrist, a pediatrician, a psychologist, a clinical psychologist, a psychiatric nurse, a psychiatric nurse practitioner, a nurse practitioner, an advanced psychiatric nurse specialist, a mental health specialist, a neurologist, a speech therapist, an occupational therapist, or a pathologist.

Administration of THC to a Human

Generally, an individual diagnosed with ADHD or ASD can be prescribed an appropriate dose of THC by a licensed health care professional, for example, any of the professionals mentioned directly above, as long as the professional is, by law, allowed to prescribe THC. THC can also be obtained "over the counter" in a number of states where it is legal to purchase THC recreationally.

Dosing

The dose is the amount of drug taken at any one time. This can be expressed as the weight of drug (e.g. 2.5 mg), volume of drug solution (e.g. 1 mL, 2 drops), the number of dosage forms (e.g. 1 capsule), or some other quantity. The dosage regimen is the frequency at which the drug doses are given. Examples include 2.5 mL twice a day, or one tablet three times a day. The total daily dose is calculated from the dose and the number of times per day the dose is taken. The optimal dosage is the dosage that gives the desired effect with minimum side effects.

The dosage form is the physical form of a dose of drug. Common dosage forms include tablets, capsules, creams, ointments, aerosols, edible formulations, and patches. Each dosage form may also have a number of specialized forms such as extended-release, buccal, dispersible and chewable tablets. The strength is the amount of drug in the dosage form or a unit of the dosage form (e.g. 50 mg capsule, 25 mg/5 mL suspension). The route of administration is the way the dosage form is given. Common routes of administration include oral, rectal, inhalation, nasal and topical.

As mentioned above, oral administration is an effective mode of administering THC. THC can be formulated, for example, into short-acting, long-acting, or extended release varieties. In each of these varieties, the active ingredient (THC) is the same, but it is released differently in the body. Long-acting or extended release forms often allow an individual to take the medication just once a day. The phrase "extended release" means the medication is released gradually so that a controlled amount enters the body over a period of time. "Long acting" means the medication stays in the body for a long time.

There are many factors taken into consideration when deciding the dose of a drug and the dosing regimen of a drug, including, but not limited to, age, weight, sex, ethnicity, liver and kidney function, whether the patient smokes, medical condition of the patient, and the severity of the condition to be treated. Other medicines may also affect the drug dose. A physician or licensed health care professional of ordinary skill in the art can readily determine and prescribe the effective amount of the drug required to prevent, counter, arrest, or reverse the progress of the condition (or symptom or deficit). Optimal precision in achieving a concentration of drug within the range that yields efficacy without toxicity may require a regimen based on the kinetics of the drug's availability to target sites. This involves a consideration of the distribution, equilibrium, and elimination of a drug.

A common method for dose adjustment in children in pediatric clinical practice is to normalize the adult dose by body weight (e.g., mg kg-1), assuming a linear relationship between weight and dose. This means that the dose doubles with a twofold increase in the weight of a child. Another method for dose adjustment is based on age: the pediatric population is divided into subcategories (preterm newborns, term newborns, infants, toddlers, children and adolescents) and the dose is selected according to a child's age. Scaling the dose from adults can also be performed by normalization based on body surface area (BSA), under the assumption that metabolic processes in humans are constant when expressed as a function of BSA (see Cella, M. et al., British Journal of Clinical Pharmacology (2010)70:4, 597-603).

Typically, THC should be administered at the lowest effective dosage, and dosage should be adjusted according to the therapeutic needs and response of the patient under the supervision of a licensed health care professional. Once the lowest effective dose is determined, the dose can generally be increased as needed or as prescribed by a health care professional.

Elderly patients may be more sensitive to neurologic, psychoactive, and postural-hypotensive effects of THC than younger patients. Dosing of THC should be monitored by a licensed health care professional to avoid damage to the liver. A THC compound can be taken with or without food, or in an edible form. A THC compound can be taken, for example, in the morning, in the afternoon, and prior to bed. A licensed health care professional should also determine if there are interactions with any other medications or drugs that the patient is currently taking. Drug interactions may change how a medication works or increase a patient's risk for serious side effects. Any adverse effects, such as nausea, seizure, vomiting, tremors, hypertension, should be monitored by the patient, and the patient's health care provider promptly notified.

THC may be administered to a child or an adult. For example, a child from 3 to 17 years old, or and adult from 18 years old and above.

THC may be administered as a single daily dose, or the total daily dosage may be administered in divided doses of, for example, two, three, four, or five or more times a day. A single dose of THC can be taken, for example, every 2 to 4 hours, every 4 to 6 hours, every 6-8 hours, every 8 to 10 hours, or every 12 hours.

A dose of THC can be formulated as a time-release dose, for example, a time-release capsule. THC can be administered to a human such that a certain dose is maintaining over a period of time, for example, any portion of a 24-hour period, a 24-hour period, a day, or continuously, based on the weight of the human.

Provided below are exemplary mg/kg doses and mg doses of effective amounts of THC, for use in the treatment of ASD, ADHD, or both, or the treatment of one or more deficits associated with either ASD, or ADHD, or the treatment of a comorbid condition with either ASD or ADHD.

For example, a 25 pound human (11.3 kg), can take from 0.08 mg/kg to 88.5 mg/kg in one or more doses per day. For example, a 50 pound human (22.67 kg), can take from 0.04 mg/kg to 44.11 mg/kg in one or more doses per day. For example, a 100 pound human (45.36 kg), can take from 0.02 mg/kg to 23.06 mg/kg in one or more doses per day. For example, a 150 pound human (68.04 kg), can take from 0.01 mg/kg to 14.69 mg/kg in one or more doses per day. For example, a 200 pound human (90.72 kg), can take from 0.01 mg/kg to 11.02 mg/kg in one or more doses per day. For example, a 250 pound human (113.4 kg), can take from 0.008 mg/kg to 8.82 mg/kg in one or more doses per day. For example, a 300 pound human (136.1 kg), can take from 0.007 mg/kg to 7.35 mg/kg in one or more doses per day. For example, a 500 pound human (226.8 kg), can take from 0.004 mg/kg to 4.41 mg/kg in one or more doses per day. One of skill in the art could easily calculate the proper dose based on the human's weight and determine the optimal dosage regimen (for example, 3 times a day).

THC can be administered to the human at a dose of 0.001 mg/kg to 0.01 mg/kg, 0.01 mg/kg to 0.1 mg/kg, 0.1 mg/kg to 1 mg/kg, 1 mg/kg to 2 mg/kg, 2 mg/kg to 3 mg/kg, 3 mg/kg to 4 mg/kg, 4 mg/kg to 5 mg/kg, 5 mg/kg to 6 mg/kg, 6 mg/kg to 7 mg/kg, 7 mg/kg to 8 mg/kg, 8 mg/kg to 9 mg/kg, 9 mg/kg to 10 mg/kg, 10 mg/kg to 11 mg/kg, 11 mg/kg to 12 mg/kg, 12 mg/kg to 13 mg/kg, 13 mg/kg to 14 mg/kg, 14 mg/kg to 15 mg/kg, 15 mg/kg to 20 mg/kg, 20 mg/kg to 25 mg/kg, 25 mg/kg to 30 mg/kg, 30 mg/kg to 35 mg/kg, 35 mg/kg to 40 mg/kg, 40 mg/kg to 45 mg/kg, or more than 45 mg/kg, based on the weight of the human. The dose can be repeated one or more times per a specified period of time, for example, every 4 hours, every 6 hours or every 12 hours (one or more times per day).

A single dose of THC can be, for example, 0.1 mg/kg to 1 mg/kg, 1 mg/kg to 2 mg/kg, 2 mg/kg to 3 mg/kg, 3 mg/kg to 4 mg/kg, 4 mg/kg to 5 mg/kg, 5 mg/kg to 6 mg/kg, 6 mg/kg to 7 mg/kg, 7 mg/kg to 8 mg/kg, 8 mg/kg to 9 mg/kg, 9 mg/kg to 10 mg/kg, 10 mg/kg to 11 mg/kg, 11 mg/kg to 12 mg/kg, 12 mg/kg to 13 mg/kg, 13 mg/kg to 14 mg/kg, 14 mg/kg to 15 mg/kg, or above 15 mg/kg based on the weight of the human.

A single dose of THC can be, for example, 2.5 mg, 5 mg, 10 mg, 15 mg, 25 mg, or 30 mg, from about 25 mg to about 35 mg, or from about 35 to about 50 mg. A single dose of a THC can also be: from 1 to 5 mg, from 5 to 10 mg, from 10 mg to 20 mg, from 20 mg to 30 mg, from 30 mg to 40 mg, from 40 mg to 50 mg, from 50 mg to 60 mg, from 60 mg to 70 mg, from 70 mg to 80 mg, from 80 mg to 90 mg, from 90 mg to 100 mg, from 100 mg to 110 mg, from 110 mg to 120 mg, from 120 mg to 130 mg, from 130 mg to 140 mg, from 140 mg to 150 mg, from 150 mg to 200 mg, from 200 mg to 250 mg, from 250 mg to 300 mg, from 300 mg to 350 mg, from 350 mg to 500 mg, of from 500 mg to 1,000 mg, or 1,000 mg or above.

A dose of THC can be administered with a dose of an additional compound or drug. For example, a dose of THC can be administered with a dose of CBD. A dose of THC can be administered with a dose of caffeine, or another substance commonly prescribed to treat symptoms occurring in ASD and ADHD patients such as a selective serotonin reuptake inhibitor (SSRI).

A single dose of CBD taken together with THC can be, for example, from 1 to 5 mg, from 5 to 10 mg, from 10 mg to 20 mg, from 20 mg to 30 mg, from 30 mg to 40 mg, from 40 mg to 50 mg, from 50 mg to 60 mg, from 60 mg to 70 mg, from 70 mg to 80 mg, from 80 mg to 90 mg, from 90 mg to 100 mg, from 100 mg to 110 mg, from 110 mg to 120 mg, from 120 mg to 130 mg, from 130 mg to 140 mg, from 140 mg to 150 mg, from 150 mg to 200 mg, from 200 mg to 250 mg, from 250 mg to 300 mg, from 300 mg to 350 mg, or from 350 mg to 500 mg.

The time of onset of the effects of a single dose of THC, the time in which a maximum effect is reached, and the duration of the effect of THC, will depend on the dosage of THC give to the patient (human).

For example, the onset of a single dose of THC can be, for example, approximately 30-90 minutes after taking the drug, reach a maximum effect after 2-3 hours, and last for approximately 4-12 hours depending on the dose.

For example, the onset of a single dose of THC can be, for example, approximately 30-60 minutes after taking the drug, reach a maximum effect after 2-3 hours, and last for approximately 4 to 8 hours depending on the dose.

For example, the onset of a single dose of THC can be, for example, approximately 15-120 minutes after taking the drug, reach a maximum effect after 1-4 hours, and last for approximately 4-12 hours depending on the dose.

In pharmacology, the international unit (IU) is a unit of measurement for the amount of a substance (e.g. THC). The mass or volume that constitutes one international unit varies based on which substance is being measured, and the variance is based on the biological activity or effect, for the purpose of easier comparison across substances. International units are used to quantify drugs, for example THC. An IU is a quantity of a biologic (such as THC) that produces a particular biological effect agreed upon as an international standard. IU is dependent on the potency of the substance, and each substance would have a different IU to milligram conversion. Many biological agents exist in different forms or preparations. The goal of the IU is to be able to compare these, so that different forms or preparations with the same biological effect will contain the same number of IUs.

Therapeutically Effective Amount of THC

A "therapeutically-effective amount" according to the present disclosure, means that the dose of the therapeutic agent(s) (e.g. THC or THC and CBD) is such that a therapeutic level is delivered to the bloodstream over the term that the THC is to be used. Such delivery is dependent on a number of variables including the time period for which the individual dosage unit is to be used, or the flux rate of the therapeutic agent into the systemic circulation of the subject. For example, the term "therapeutically effective amount of THC" as used herein means an amount of THC sufficient to treat a human with ASD or ADHD. Alternatively, the term "therapeutically effective amount of THC" means an amount of THC sufficient to treat, limit, ameliorate, prevent, reduce, delay and/or improve one or more deficits associated with ASD or ADHD.

Toxicity and therapeutic efficacy of the therapeutic agent(s) (and hence the dosing) of THC can be determined by standard pharmaceutical procedures, for example, for determining LD50 (the dose lethal to 50% of the population) and the ED50 (the dose therapeutically effective in 50% of the population). The dose ratio between toxic and therapeutic effects is the therapeutic index and it can be expressed as the ratio LD50/ED50.

The dose administered to a human should be sufficient to affect a therapeutic response over a specified time frame.

Formulations

THC compounds of the present disclosure that can be formulated for use in the treatment of ASD, ADHD, or a comorbid condition of ASD or ADHD, can be an isomer of tetrahydrocannabinol, a stereoisomer of tetrahydrocannabinol, a trans isomer of tetrahydrocannabinol, a derivative of tetrahydrocannabinol, a metabolite of tetrahydrocannabinol (for example, 11-OH-THC, 11-COOH-THC, 11-OH-delta 9 THC, or 11-nor-delta-9-THC-9-carboxylic acid (11-nor-acid)), delta-9-THC, or a synthetic tetrahydrocannabinol. THC can be chemically synthesized or extracted from *Cannabis sativa* L. (marijuana).

The THC compounds of the present disclosure can be administered orally. THC can be administered, for example, in a tablet, capsule, caplet, pill, lozenge, chewable, or troche. THC may also be delivered as an "edible", employing one or more foods or ingredients as a vehicle of administration. An edible can be, for example, in the form of a cookie, a bar, or a lozenge.

The THC compounds of the present disclosure can be administered via oral mucosal administration, for example, in a liquid form. The oral mucosa is highly vascularized such that drugs that are absorbed through the oral mucosa directly enter the systemic circulation, bypassing the gastrointestinal tract and first-pass metabolism in the liver.

Pharmaceutical compositions suitable for use in methods of the present disclosure can include one or more conventional nontoxic pharmaceutically acceptable excipients such as fillers, binders, carriers, adjuvants, and/or vehicles as desired. Carrier materials that can be employed are any of those commonly used excipients in pharmaceutics and should be selected on the basis of compatibility with the form of THC being used and the release profile properties of the desired dosage form or composition. Non-limiting examples of suitable pharmaceutically acceptable excipients include binders, disintegration agents, filling agents, surfactants, pH correcting agents, stabilizers, lubricants, diluents, anti-adherents, glidants, carriers, etc.

Non-limiting examples of suitable pharmaceutically compatible carriers include acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, or pregelatinized starch, and the like.

Additionally, drug formulations are discussed in, for example, Remington's, The Science and Practice of Pharmacy (2000) Lieberman, H. A. and Lachman, L., Eds., Pharmaceutical Dosage Forms, Marcel Decker, New York, N.Y., 1980; and Liebeman, H. A., et al., Pharmaceutical Dosage Forms (Volumes 1-3, 1990).

For instance, for oral administration in the form of a tablet or capsule, the active drug component can be combined with, for example, ethanol, glycerol, water and the like. A capsule containing an active compound can be prepared by mixing the active compound of the present disclosure with, for example, lactose and magnesium stearate, calcium stearate, starch, or talc, and placing the mixture in a gelatin capsule. Tablets may be prepared by mixing the active ingredient with conventional tableting ingredients such as calcium phosphate, lactose, cornstarch or magnesium stearate.

The liquid form of the drug can be in suitably flavored suspending or dispersing agents such as the synthetic and natural gums, for example, tragacanth, acacia, methyl-cellulose and the like. Other dispersing agents, which may be employed, include glycerin and the like.

In oral drug delivery, known colloidal deliver systems can be used to enhance the bioaccessibility of a THC edible. For example, applications of lipid and polymeric colloidal particles, liposomes, micelles, and microemulsions have been used for efficient delivery of drug molecules.

Methods of Determining or Measuring the Effects of THC on a human with ADHD or ASD The effectiveness of THC to treat a human with ASD or ADHD, or the effectiveness of THC to treat one or more deficits associated with ASD or ADHD can be determined using observation or diagnostics (e.g. tests). The effect of THC on a human can be determined by observation only. For example, an improvement in a deficit in oral communication can be observed in a human that is being treated with a specific dose of a THC. Or an increase in attentiveness, or a decrease in hyperactivity can be observed in a human being treated with a specific dose of THC. Alternatively, the effectiveness of THC to treat a human with ASD or ADHD, or the effectiveness of THC to treat one or more deficits associated with ASD or ADHD can be determined using any method known to one of skill in the art.

Exemplary methods or types of tests (tasks) are psychiatric, psychosocial, educational, cognitive function, psychopathology, social functioning, and adaptive behavior. Exemplary timing tasks are described in Noreika (cited above). Exemplary motor response tasks are described in Ben-Pazi 2003 and Ben-Pazi 2006 (cited above). Exemplary tasks are also described below.

Two-component instrumental discrimination task, as disclosed, for example, in the following articles: Han, C. J. and Robinson, J. K., Behavioral Neuroscience (2001) 115(1): 243-246; Mallet, P. E. and Beninger, R. J., Psychopharmacology (Berl) (1998) 140(1):11-19; Nava, F., et al., Br J Pharmacol (2000) 130(6):1201-1210; Winsauer, P. J., et al., Behav Pharmacol (1999) 10(5):497-511; and Zimmerberg, B., et al., Nature (1971) 233(5318):343-345.

Time interval estimation task based on a fixed-interval schedule, as disclosed, for example, in the following articles: Han, C. J. and Robinson, J. K., Behavioral Neuroscience (2001) 115(1):243-246; Mallet, P. E. and Beninger, R. J., Psychopharmacology (Berl) (1998) 140(1):11-19; Nava, F., et al., Br J Pharmacol (2000) 130(6):1201-1210; Winsauer, P. J., et al., Behav Pharmacol (1999) 10(5):497-511; and Zimmerberg, B., et al., Nature (1971) 233(5318):343-345.

Conditional discriminations, as disclosed, for example, in the following articles: Han, C. J. and Robinson, J. K., Behavioral Neuroscience (2001) 115(1):243-246; Mallet, P. E. and Beninger, R. J., Psychopharmacology (Berl) (1998) 140(1):11-19; Nava, F., et al., Br J Pharmacol (2000) 130 (6):1201-1210; Winsauer, P. J., et al., Behav Pharmacol (1999) 10(5):497-511; and Zimmerberg, B., et al., Nature (1971) 233(5318):343-345.

Two-task procedure tasks, as disclosed, for example, in the following articles: Han, C. J. and Robinson, J. K., Behavioral Neuroscience (2001) 115(1):243-246; Mallet, P. E. and Beninger, R. J., Psychopharmacology (Berl) (1998) 140(1):11-19; Nava, F., et al., Br J Pharmacol (2000) 130 (6):1201-1210; Winsauer, P. J., et al., Behav Pharmacol (1999) 10(5):497-511; and Zimmerberg, B., et al., Nature (1971) 233(5318):343-345.

Child Behavior Checklist (CBCL), as described, for example, in Ronald, A., et al. (2010) Exploring the relationship between autistic-like traits and ADHD behaviors in early childhood: findings from a community twin study of 2-year olds, J. Abnorm. Child Psychol. 38, 185-196.

Confirmatory Factor Analysis (CFA), as described, for example, in Lecavalier, L., et al. (2009) Validation of DSM-IV model of psychiatric syndromes in children with autism spectrum disorders, J. Autism Dev. Disord. 39, 278-289.

Pediatric Quality of Life Inventory (PedsQL)™, as described in Varni, J. W., et al, Med Care (1999) 37(2):126-139.

Vineland Adaptive Behavior Scales (VABS-II), as described in Vineland Adaptive Behavior Scales, Second Edition (VinelanndTM-II) by Sara S. Sparrow, Ph.D., Domenic V. Cicchetti, Ph.D., and David A. Balla.

Kaufman Assessment Battery for Children, Second Edition (KABCTM-II) by Alan S. Kaufman, Ph.D., and Nadeen L. Kaufman, EdD.

Parent and Teacher Referenced Rating Scale (ECI-4), as described, for example, in Mulligan, A., et al. (2009) Autism symptoms in attention-deficit/hyperactivity disorder: a familial trait which correlates with conduct, oppositional defiant, language and motor disorders, J. Autism Dev. Disord. 39,197-209.

Kiddle Schedule for Affective Disorders and Schizophrenia-Epidemiologic Version, as described in, for example, Orvaschel H., Schedule for Affective Disorders and Schizophrenia for School-Age Children Epidemiologic Version, 5th ed. Ft. Lauderdale, Fla., Nova Southeastern University, Center for Psychological Studies, 1994, and Orvaschel H., Psychiatric interviews suitable for use in research with children and adolescents, Psychopharmacol Bull. 1985; 21(4):737-745.

Social Adjustment Inventory for Children and Adolescents (SAICA), as described in, John, K., et al., The Social Adjustment Inventory for Children and Adolescents (SAICA): testing of a new semistructured interview, J Am Acad Child Adolesc Psychiatry (1987) 26(6):898-911; Reynolds, C. R., Critical measurement issues in learning disabilities, J Spec Educ. (1984) 18(4):451-475; and Faraone, S. V., et al., Intellectual performance and school failure in children with attention deficit hyperactivity disorder and in their siblings, J Abnorm Psychol. (1993) 102(4):616-623.

Moos Family Environment Scale, as described in, Moos, R. H. and Moos, B. S., Manual for the Family Environment Scale, Palo Alto, Calif., Consulting Psychologists Press, 1974.

Intelligence Scale for Children-Revised (WISC-R) and the Wisconsin Card Sorting Test, as described in: Wechsler, D., Manual for the Wechsler Intelligence Scale for Children-Revised, New York, N.Y., The Psychological Corporation, 1974; Grant, D. A. and Berg, E. A., The Wisconsin Card Sorting Test. Odessa, Fla.: Psychological Assessment Resources; 1948; and Sattler J. Psychological Assessment, 4th ed. New York, NY: McGraw-Hill; 1988.

Cognitive Functioning: Stanford-Binet Intelligence Scales, 5th edition (SB-5), as described in Roid, G. H., Stanford-Binet Intelligence Scales, 5th, Itasca, Ill.: Riverside Publishing; and Mullen Scales of Early Learning (MSEL), as described in Mullen, E. M. Mullen: Scales of Early Learning, Circle Pines, Minn.: American Guidance Service, Inc; 1995.

Psychopathology: The BASC-2, as described in Reynolds, C R. and Kamphaus, R. W., Behavior Assessment System for Children, 2nd, Minneapolis, Minn.: Pearson, Inc; 2004.

Social Functioning and Autism-related Mannerisms: The Social Responsiveness Scale (SRS) as described in Constantino, J. N. and Gruber, C. P. Social Responsiveness Scale, Los Angeles, Calif.: Western Psychological Services; 2005.

Adaptive Behavior: The Vineland Adaptive Behavior Scales, Second edition (VABS-II) as described in Sparrow, S. S., et al., The Vineland Adaptive Behavior Scale, 2nd, Minneapolis, Minn.: Pearson Assessment, 2007.

As discussed above and as shown in the Examples section below, THC improves symptoms and deficits associated with ASD and ADHD, including without limitation the following categories of symptoms and deficits: 1) deficits in hyperactivity, impulsivity and inattention (including cognitive and behavioral impairments resulting therefrom); 2) timing deficits; 3) deficits in social interaction; 4) deficits in controlling repetitive-behaviors; 5) deficits in oral communication skills; 6) deficits in motor skills; 7) deficits in visual/spatial problem solving; and 8) deficits in sensory processing.

Baseline measures of deficits and symptoms can be obtained through reports from patients and other sources including, for example, families, therapists, physicians, caretakers and teachers. Baseline measures of symptoms and deficits can also be obtained using currently-accepted diagnostic procedures, including without limitation those tests specifically identified above. Baseline measures in deficits and symptoms can also be obtained through observation of the patient engaging in routine daily activities such as walking, speaking and otherwise interacting with others, as well as observation of the patient performing tasks requiring fine-motor skills such as threading a needle, drawing, or writing in cursive.

After an adjustment period of approximately 1-2 weeks to allow the patient to acclimate to the effects of THC, ASD and ADHD patients should exhibit fewer and less severe ASD and ADHD-related symptoms and deficits and, in particular, should experience fewer and less severe manifestations of the symptoms and deficits identified above.

Comorbity

The term "comorbidity", as used herein, describes two or more disorders, symptoms, or conditions occurring in the same person. They can occur at the same time or one after the other. THC is effective to treat ASD and/or ADHD in combination with any one or more of the following comorbid psychological disorders, symptoms, or conditions described herein. THC is also effective at treating comorbid psychological disorders, symptoms and conditions even when those disorders, symptoms and conditions occur independently of ADHD and ASD. Oral administration of THC is effective to treat ASD and/or ADHD in combination with any one or more of the following comorbid psychological disorders, symptoms, or conditions described herein. Oral administration of THC is also effective at treating comorbid psychological disorders, symptoms and conditions even when those disorders, symptoms and conditions occur independently of ADHD and ASD.

As described in the DSM-5, in regards to autism spectrum disorder, under the section entitled "Comorbity", "[a]utism spectrum disorder is frequently associated with intellectual impairment and structural language disorder (e.g., an inability to comprehend and construct sentences with proper grammar). Many individuals with autism spectrum disorder also have psychiatric symptoms that do not form part of the diagnostic criteria for the disorder (about 70% of individuals with autism spectrum disorder may have one comorbid mental disorder, and 40% may have two or more comorbid mental disorders). When criteria for both ADHD and autism spectrum disorder are met, both diagnoses may be given. The same principal applies to concurrent diagnoses of autism spectrum disorder and developmental coordination disorder, anxiety disorders, depressive disorders, and other comorbid diagnoses. Specific learning difficulties (literacy and numeracy) are common, as is developmental coordination disorder."

As described in the DSM-5, in regards to attention-deficit/hyperactivity disorder, under the section entitled "Comorbity", the DSM-5 states that "[i]n clinical setting, comorbid disorders are frequent in individuals whose symptoms meet criteria for ADHD. In the general population, oppositional defiant disorder co-occurs with ADHD in approximately half of children with the combined presentation and about a quarter with the predominantly inattentive presentation. Conduct disorder co-occurs in about a quarter of children or adolescents with the combined presentation, depending on age and setting. Most children and adolescents with disruptive mood dysregulation disorder have symptoms that also meet criteria for ADHD; a lesser percentage of children with ADHD have symptoms that meet criteria for disruptive mood dysregulation disorder. Specific learning disorder commonly co-occurs with ADHD. Anxiety disorders and major depressive disorder occur in a minority of individuals with ADHD but more often than in the general population. Intermittent explosive disorder occurs in a minority of adults with ADHD, but at rates above population levels. In adults, antisocial and other personality disorders may co-occur with ADHD. Other disorders that may co-occur with ADHD include obsessive-compulsive disorders, tic disorders, and autism spectrum disorder."

Biederman, J., et al., Am J Psychiatry (1991) 148(5) 564-577, discusses numerous studies showing that ADHD is comorbid with conduct disorders, oppositional defiant disorders, mood disorders, anxiety disorders, learning disabilities, and other conditions Anxiety and depression are often comorbid with ADHD, for example, as described in: Cantwell, D. P. (1996) Attention deficit disorder: a review of the past 10 years, J. Am. Acad. Child Adolesc. Psychiatry 35, 978-98710.1097/00004583-199608000-00008; Biederman, J., et al. (1991) Comorbidity of attention deficit hyperactivity disorder with conduct, depressive, anxiety, and other disorders, Am. J. Psychiatry 148, 564-577; Eiraldi, R. B., et al. (2000) Assessing ADHD and comorbid disorders in children: the Child Behavior Checklist and the Devereux Scales of Mental Disorders. J. Clin. Child Psychol. 29, 3-1610.1207/S15374424jccp2901_2); and Antshel, K. M. and Remer, R. (2003) Social skills training in children with attention deficit hyperactivity disorder: a randomized-controlled clinical trial, J. Clin. Child Adolesc. Psychol. 32, 153-16510.1207/15374420360533149). An exemplary list of comorbid disorders, symptoms, or conditions that can present in ADHD or ASD are provided below.

Specific Learning Disorders
Motor Disorders
Other Neurodevelopmental Disorders
Major Depressive Disorder
Persistent Depressive Disorder
Dysthemia
Substance/Medication-Induced Depressive Disorder
Depressive Disorder Due to Another Medical Condition
Other Specified Depressive Disorder
Unspecified Depressive Disorder
Separation Anxiety Disorder
Selective Mutism
Specific Phobias
Social Anxiety Disorder
Panic Disorder
Agoraphobia
Generalized Anxiety Disorder
Substance/Medication/Induced Anxiety Disorder
Anxiety Disorder Due to Another Medical Condition
Unspecified Anxiety Disorder
Obsessive-Compulsive Disorder
Body Dysmorphic Disorder
Hoarding Disorder
Trichotillomania
Excoriation (Skin-picking) Disorder
Substance/Medication-Induced Obsessive-Compulsive and Related Disorder
Obsessive-Compulsive and Related Disorder Due to Another Medical Condition
Other Specified Obsessive-Compulsive and Related Disorder
Reactive Attachment Disorder
Disinhibited Social Engagement Disorder
Acute Stress Disorder
Adjustment Disorders
Rumination Disorder
Enuresis
Encopresis
Other Specified Elimination Disorder
Unspecified Elimination Disorder
Insomnia Disorder
Circadian Rhythm Sleep-Wake Disorders
Non-Rapid Eye Movement Sleep Arousal Disorders
Nightmare Disorder
Rapid Eye Movement Sleep Behavior Disorder
Substance/Medication-Induced Sleep Disorder
Other Specified Insomnia Disorder
Unspecified Insomnia Disorder
Other Specified Hypersomnolence Disorder
Other Specified Sleep-Wake Disorder
Unspecified Sleep-Wake Disorder
Oppositional Defiant Disorder
Intermittent Explosive Disorder
Conduct Disorder
Antisocial Personality Disorder
Pyromania
Kleptomania
Other Specified Disruptive, Impulse-Control, and Conduct Disorders
Unspecified Disruptive, Impulse Control, and Conduct Disorder.
All Substance-Related and Addictive Disorders (such as stimulants, depressants and alcohol)
Gambling Disorder
Major or Mild Neurocognitive Disorders
Paranoid Personality Disorder
Some types of Schizoid Personality Disorder (non-schizophrenic)
Shizotypal Personality Disorder
Antisocial Personality Disorder
Borderline Personality Disorder
Histrionic Personality Disorder
Narcissistic Personality Disorder
Avoidant Personality Disorder
Dependent Personality Disorder
Obsessive-Compulsive Personality Disorder
Other Specified Personality Disorder
Unspecified Personality Disorder
Paraphilic Disorders
Bipolar
Cyclothemic
Social (Pragmatic) Communication Disorder As shown in the Examples section below, THC is effective at treating the comorbid conditions of anxiety, depression, obsessive-compulsive disorder, and substance abuse.

In one aspect, some embodiments relate to a method of treating a human with autism spectrum disorder (ASD) including administering a therapeutically effective amount of tetrahydrocannabinol (THC) to the human. In some embodiments, THC is administered orally. In some embodiments, the oral administration is a capsule, caplet, tablet, or an edible. In some embodiments, the capsule, caplet, tablet, or edible is a time-release capsule, caplet, tablet, or edible. In some embodiments, the capsule, caplet, tablet, or edible includes THC at a dose of 0.001 mg/kg to 0.01 mg/kg, 0.01 mg/kg to 0.1 mg/kg, 0.1 mg/kg to 1 mg/kg, 1 mg/kg to 2 mg/kg, 2 mg/kg to 3 mg/kg, 3 mg/kg to 4 mg/kg, 4 mg/kg to 5 mg/kg, 5 mg/kg to 6 mg/kg, 6 mg/kg to 7 mg/kg, 7 mg/kg to 8 mg/kg, 8 mg/kg to 9 mg/kg, 9 mg/kg to 10 mg/kg, 10 mg/kg to 11 mg/kg, 11 mg/kg to 12 mg/kg, 12 mg/kg to 13 mg/kg, 13 mg/kg to 14 mg/kg, 14 mg/kg to 15 mg/kg, 15 mg/kg to 20 mg/kg, 20 mg/kg to 25 mg/kg, 25 mg/kg to 30 mg/kg, 30 mg/kg to 35 mg/kg, 35 mg/kg to 40 mg/kg, 40 mg/kg to 45 mg/kg, or more than 45 mg/kg, based on the human's weight. In some embodiments, the capsule, caplet, tablet, or edible includes 2.5 mg THC, 5 mg THC, 10 mg THC, 15 mg THC, 25 mg THC, 30 mg THC, from about 25 mg THC to about 35 mg THC, or from about 35 mg THC to about 50 mg of THC. In some embodiments, the capsule, caplet, tablet, or edible includes 1 mg to 5 mg, from 5 mg to 10 mg, from 10 mg to 20 mg, from 20 mg to 30 mg, from 30 mg to 40 mg, from 40 mg to 50 mg, from 50 mg to 60 mg, from 60 mg to 70 mg, from 70 mg to 80 mg, from 80 mg to 90 mg, from 90 mg to 100 mg, from 100 mg to 110 mg, from 110 mg to 120 mg, from 120 mg to 130 mg, from 130 mg to 140 mg, from 140 mg to 150 mg, from 150 mg to 200 mg, from 200 mg to 250 mg, from 250 mg to 300 mg, from 300 mg to 350 mg, from 350 mg to 500 mg, from 500 mg to 1,000 mg, or 1,000 mg or above of THC.

In some embodiments, the oral administration of THC includes a liquid. In some embodiments, the liquid includes THC at a dose of 0.001 mg/kg to 0.01 mg/kg, 0.01 mg/kg to 0.1 mg/kg, 0.1 mg/kg to 1 mg/kg, 1 mg/kg to 2 mg/kg, 2 mg/kg to 3 mg/kg, 3 mg/kg to 4 mg/kg, 4 mg/kg to 5 mg/kg, 5 mg/kg to 6 mg/kg, 6 mg/kg to 7 mg/kg, 7 mg/kg to 8 mg/kg, 8 mg/kg to 9 mg/kg, 9 mg/kg to 10 mg/kg, 10 mg/kg to 11 mg/kg, 11 mg/kg to 12 mg/kg, 12 mg/kg to 13 mg/kg, 13 mg/kg to 14 mg/kg, 14 mg/kg to 15 mg/kg, 15 mg/kg to 20 mg/kg, 20 mg/kg to 25 mg/kg, 25 mg/kg to 30 mg/kg, 30 mg/kg to 35 mg/kg, 35 mg/kg to 40 mg/kg, 40 mg/kg to 45 mg/kg, or more than 45 mg/kg, based on the human's weight. In some embodiments, the liquid includes 2.5 mg THC, 5 mg THC, 10 mg THC, 15 mg THC, 25 mg THC, 30 mg THC, from about 25 mg THC to about 35 mg THC, or from about 35 mg THC to about 50 mg of THC. In some embodiments, the liquid includes 1 mg to 5 mg, from 5 mg to 10 mg, from 10 mg to 20 mg, from 20 mg to 30 mg, from 30 mg to 40 mg, from 40 mg to 50 mg, from 50 mg to 60 mg, from 60 mg to 70 mg, from 70 mg to 80 mg, from 80 mg to 90 mg, from 90 mg to 100 mg, from 100 mg to 110 mg, from 110 mg to 120 mg, from 120 mg to 130 mg, from 130 mg to 140 mg, from 140 mg to 150 mg, from 150 mg to 200 mg, from 200 mg to 250 mg, from 250 mg to 300 mg, from 300 mg to 350 mg, from 350 mg to 500 mg, from 500 mg to 1,000 mg, or 1,000 mg or above of THC.

In some embodiments, the treatment method further includes administration of cannabidiol (CBD), caffeine, or a selective serotonin reuptake inhibitor (SSRI) to the human. In some embodiments, the administering is one time per day, two times per day, three times per day, four times per day, five times per day, or six or more times per day. In some embodiments, the human is 3-17 years old, or 18 years old or above. In some embodiments, in addition to treating ASD, one or more comorbid symptoms, disorders, or conditions is also treated. In some embodiments, the one or more comorbid symptoms is selected from the group consisting of anxiety, depression, obsessive-compulsive disorder (OCD), substance abuse, or a combination thereof.

In one aspect, some embodiments relate to a method of treating a human with autism spectrum disorder (ASD) which includes administering a therapeutically effective amount of tetrahydrocannabinol (THC) to the human. In some embodiments, THC is administered orally. In some embodiments, the oral administration includes a capsule, caplet, tablet, or an edible. In some embodiments, the capsule, caplet, tablet, or edible is a time-released capsule, caplet, tablet, or edible. In some embodiments, the capsule, caplet, tablet, or edible includes THC at a dose of 0.001 mg/kg to 0.01 mg/kg, 0.01 mg/kg to 0.1 mg/kg, 0.1 mg/kg to 1 mg/kg, 1 mg/kg to 2 mg/kg, 2 mg/kg to 3 mg/kg, 3 mg/kg to 4 mg/kg, 4 mg/kg to 5 mg/kg, 5 mg/kg to 6 mg/kg, 6 mg/kg to 7 mg/kg, 7 mg/kg to 8 mg/kg, 8 mg/kg to 9 mg/kg, 9 mg/kg to 10 mg/kg, 10 mg/kg to 11 mg/kg, 11 mg/kg to 12 mg/kg, 12 mg/kg to 13 mg/kg, 13 mg/kg to 14 mg/kg, 14 mg/kg to 15 mg/kg, 15 mg/kg to 20 mg/kg, 20 mg/kg to 25 mg/kg, 25 mg/kg to 30 mg/kg, 30 mg/kg to 35 mg/kg, 35 mg/kg to 40 mg/kg, 40 mg/kg to 45 mg/kg, or more than 45 mg/kg, based on the human's weight. In some embodiments, the capsule, caplet, tablet, or edible includes 2.5 mg THC, 5 mg THC, 10 mg THC, 15 mg THC, 25 mg THC, 30 mg THC, from about 25 mg THC to about 35 mg THC, or from about 35 mg THC to about 50 mg of THC. In some embodiments, the capsule, caplet, tablet, or edible includes 1 mg to 5 mg, from 5 mg to 10 mg, from 10 mg to 20 mg, from 20 mg to 30 mg, from 30 mg to 40 mg, from 40 mg to 50 mg, from 50 mg to 60 mg, from 60 mg to 70 mg, from 70 mg to 80 mg, from 80 mg to 90 mg, from 90 mg to 100 mg, from 100 mg to 110 mg, from 110 mg to 120 mg, from 120 mg to 130 mg, from 130 mg to 140 mg, from 140 mg to 150 mg, from 150 mg to 200 mg, from 200 mg to 250 mg, from 250 mg to 300 mg, from 300 mg to 350 mg, from 350 mg to 500 mg, from 500 mg to 1,000 mg, or 1,000 mg or above of THC.

In some embodiments, the oral administration includes a liquid. In some embodiments, the liquid includes THC at a dose of 0.001 mg/kg to 0.01 mg/kg, 0.01 mg/kg to 0.1 mg/kg, 0.1 mg/kg to 1 mg/kg, 1 mg/kg to 2 mg/kg, 2 mg/kg to 3 mg/kg, 3 mg/kg to 4 mg/kg, 4 mg/kg to 5 mg/kg, 5 mg/kg to 6 mg/kg, 6 mg/kg to 7 mg/kg, 7 mg/kg to 8 mg/kg, 8 mg/kg to 9 mg/kg, 9 mg/kg to 10 mg/kg, 10 mg/kg to 11 mg/kg, 11 mg/kg to 12 mg/kg, 12 mg/kg to 13 mg/kg, 13 mg/kg to 14 mg/kg, 14 mg/kg to 15 mg/kg, 15 mg/kg to 20 mg/kg, 20 mg/kg to 25 mg/kg, 25 mg/kg to 30 mg/kg, 30 mg/kg to 35 mg/kg, 35 mg/kg to 40 mg/kg, 40 mg/kg to 45 mg/kg, or more than 45 mg/kg, based on the human's weight. In some embodiments, the wherein the liquid includes 2.5 mg THC, 5 mg THC, 10 mg THC, 15 mg THC, 25 mg THC, 30 mg THC, from about 25 mg THC to about 35 mg THC, or from about 35 mg THC to about 50 mg of THC. In some embodiments, the liquid includes 1 mg to 5 mg, from 5 mg to 10 mg, from 10 mg to 20 mg, from 20 mg to 30 mg, from 30 mg to 40 mg, from 40 mg to 50 mg, from 50 mg to 60 mg, from 60 mg to 70 mg, from 70 mg to 80 mg, from 80 mg to 90 mg, from 90 mg to 100 mg, from 100 mg to 110 mg, from 110 mg to 120 mg, from 120 mg to 130 mg, from 130 mg to 140 mg, from 140 mg to 150 mg, from 150 mg to 200 mg, from 200 mg to 250 mg, from 250 mg to 300 mg, from 300 mg to 350 mg, from 350 mg to 500 mg, from 500 mg to 1,000 mg, or 1,000 mg or above of THC. In some embodiments, the treatment method includes administration of cannabidiol (CBD), caffeine, or a selective serotonin reuptake inhibitor (SSRI) to the human. In some embodiments, the administering is one time per day, two times per day, three times per day, four times per day, five times per day, or six or more times per day. In some embodiments, the human is 3-17 years old, or 18 years old or above. In some embodiments, in addition to treating ASD, one or more comorbid symptoms, disorders, or conditions is also treated. In some embodiments, the one or more comorbid symptoms can be anxiety, depression, obsessive-compulsive disorder (OCD), substance abuse, or a combination thereof.

In one aspect, some embodiments relate to a method of treating one or more deficits in a human with autism spectrum disorder (ASD) which includes administering a therapeutically effective amount of a tetrahydrocannabinol (THC) to the human. In some embodiments, the deficit is in social communication, social interaction, or a restrictive or repetitive pattern of behavior, interest, or activity, or a combination thereof. In some embodiments, the deficit is social communication, oral communication, social interaction, interpreting body language, nonverbal communication, developing, maintaining, or understanding relationships, social-emotional reciprocity, restrictive behavior, repetitive thought, repetitive behavior, inattention, hyperactivity, impulsivity, sensory processing, timing, motor timing, perceptual timing, temporal foresight, time estimation, motor skills, visual/spatial problem solving, or a combination thereof.

In some embodiments, THC is administered orally to the human. In some embodiments, the oral administration includes a capsule, caplet, tablet, or an edible. In some embodiments, the capsule, caplet, tablet, or edible is a time-release capsule, caplet, tablet, or edible. In some embodiments, the capsule, caplet, tablet, or edible includes THC at a dose of 0.001 mg/kg to 0.01 mg/kg, 0.01 mg/kg to 0.1 mg/kg, 0.1 mg/kg to 1 mg/kg, 1 mg/kg to 2 mg/kg, 2 mg/kg to 3 mg/kg, 3 mg/kg to 4 mg/kg, 4 mg/kg to 5 mg/kg, 5 mg/kg to 6 mg/kg, 6 mg/kg to 7 mg/kg, 7 mg/kg to 8 mg/kg, 8 mg/kg to 9 mg/kg, 9 mg/kg to 10 mg/kg, 10 mg/kg to 11 mg/kg, 11 mg/kg to 12 mg/kg, 12 mg/kg to 13 mg/kg, 13 mg/kg to 14 mg/kg, 14 mg/kg to 15 mg/kg, 15 mg/kg to 20 mg/kg, 20 mg/kg to 25 mg/kg, 25 mg/kg to 30 mg/kg, 30 mg/kg to 35 mg/kg, 35 mg/kg to 40 mg/kg, 40 mg/kg to 45 mg/kg, or more than 45 mg/kg, based on the human's weight. In some embodiments, the capsule, caplet, tablet, or edible includes 2.5 mg THC, 5 mg THC, 10 mg THC, 15 mg THC, 25 mg THC, 30 mg THC, from about 25 mg THC to about 35 mg THC, or from about 35 mg THC to about 50 mg of THC. In some embodiments, the capsule, caplet, tablet, or edible includes 1 mg to 5 mg, from 5 mg to 10 mg, from 10 mg to 20 mg, from 20 mg to 30 mg, from 30 mg to 40 mg, from 40 mg to 50 mg, from 50 mg to 60 mg, from 60 mg to 70 mg, from 70 mg to 80 mg, from 80 mg to 90 mg, from 90 mg to 100 mg, from 100 mg to 110 mg, from 110 mg to 120 mg, from 120 mg to 130 mg, from 130 mg to 140 mg, from 140 mg to 150 mg, from 150 mg to 200 mg, from 200 mg to 250 mg, from 250 mg to 300 mg, from 300 mg to 350 mg, from 350 mg to 500 mg, from 500 mg to 1,000 mg, or 1,000 mg or above of THC.

In some embodiments, the oral administration includes a liquid. In some embodiments, the liquid includes THC at a dose of 0.001 mg/kg to 0.01 mg/kg, 0.01 mg/kg to 0.1 mg/kg, 0.1 mg/kg to 1 mg/kg, 1 mg/kg to 2 mg/kg, 2 mg/kg to 3 mg/kg, 3 mg/kg to 4 mg/kg, 4 mg/kg to 5 mg/kg, 5 mg/kg to 6 mg/kg, 6 mg/kg to 7 mg/kg, 7 mg/kg to 8 mg/kg, 8 mg/kg to 9 mg/kg, 9 mg/kg to 10 mg/kg, 10 mg/kg to 11 mg/kg, 11 mg/kg to 12 mg/kg, 12 mg/kg to 13 mg/kg, 13 mg/kg to 14 mg/kg, 14 mg/kg to 15 mg/kg, 15 mg/kg to 20 mg/kg, 20 mg/kg to 25 mg/kg, 25 mg/kg to 30 mg/kg, 30 mg/kg to 35 mg/kg, 35 mg/kg to 40 mg/kg, 40 mg/kg to 45 mg/kg, or more than 45 mg/kg, based on the human's weight. In some embodiments, the liquid includes 2.5 mg THC, 5 mg THC, 10 mg THC, 15 mg THC, 25 mg THC, 30 mg THC, from about 25 mg THC to about 35 mg THC, or from about 35 mg THC to about 50 mg of THC. IN some embodiments, the liquid includes 1 mg to 5 mg, from 5 mg to 10 mg, from 10 mg to 20 mg, from 20 mg to 30 mg, from 30 mg to 40 mg, from 40 mg to 50 mg, from 50 mg to 60 mg, from 60 mg to 70 mg, from 70 mg to 80 mg, from 80 mg to 90 mg, from 90 mg to 100 mg, from 100 mg to 110 mg, from 110 mg to 120 mg, from 120 mg to 130 mg, from 130 mg to 140 mg, from 140 mg to 150 mg, from 150 mg to 200 mg, from 200 mg to 250 mg, from 250 mg to 300 mg, from 300 mg to 350 mg, from 350 mg to 500 mg, from 500 mg to 1,000 mg, or 1,000 mg or above of THC.

In some embodiments, the treatment method includes administration of cannabidiol (CBD), caffeine, a selective serotonin reuptake inhibitor (SSRI), or a combination thereof. In some embodiments, the administering is one time per day, two times per day, three times per day, four times per day, five times per day, or six or more times per day. In some embodiments, the human is 3-17 years old, or 18 years old or above. In some embodiments, in addition to treating ASD, one or more comorbid symptoms, disorders, or conditions is also treated. In some embodiments, the one or more comorbid symptoms can be anxiety, depression, obsessive-compulsive disorder (OCD), substance abuse, or a combination thereof.

In one aspect, some embodiments relate to a method of treating one or more deficits in a human with Attention-Deficit/Hyperactivity Disorder (ADHD), which includes administering a therapeutically effective amount of tetrahydrocannabinol (THC) to the human. In some embodiments, the deficit is in inattention, hyperactivity, or impulsivity, which includes any associated cognitive, behavioral and motor impairments arising therefrom. In some embodiments, the deficit is social communication, oral communication, social interaction, interpreting body language, nonverbal communication, developing, maintaining, or understanding relationships, social-emotional reciprocity, restrictive behavior, repetitive thought, repetitive behavior, inattention, hyperactivity, impulsivity, sensory processing, timing, motor timing, perceptual timing, temporal foresight, time estimation, motor skills, visual/spatial problem solving, or a combination thereof.

In some embodiments, THC is administered orally. In some embodiments, the oral administration includes a capsule, caplet, tablet, or an edible. In some embodiments, the capsule, caplet, tablet, or edible is a time-release capsule, caplet, tablet, or edible. In some embodiments, the capsule, caplet, tablet, or edible includes THC at a dose of 0.001 mg/kg to 0.01 mg/kg, 0.01 mg/kg to 0.1 mg/kg, 0.1 mg/kg to 1 mg/kg, 1 mg/kg to 2 mg/kg, 2 mg/kg to 3 mg/kg, 3 mg/kg to 4 mg/kg, 4 mg/kg to 5 mg/kg, 5 mg/kg to 6 mg/kg, 6 mg/kg to 7 mg/kg, 7 mg/kg to 8 mg/kg, 8 mg/kg to 9 mg/kg, 9 mg/kg to 10 mg/kg, 10 mg/kg to 11 mg/kg, 11 mg/kg to 12 mg/kg, 12 mg/kg to 13 mg/kg, 13 mg/kg to 14 mg/kg, 14 mg/kg to 15 mg/kg, 15 mg/kg to 20 mg/kg, 20 mg/kg to 25 mg/kg, 25 mg/kg to 30 mg/kg, 30 mg/kg to 35 mg/kg, 35 mg/kg to 40 mg/kg, 40 mg/kg to 45 mg/kg, or more than 45 mg/kg, based on the human's weight. In some embodiments, the capsule, caplet, tablet, or edible includes 2.5 mg THC, 5 mg THC, 10 mg THC, 15 mg THC, 25 mg THC, 30 mg THC, from about 25 mg THC to about 35 mg THC, or from about 35 mg THC to about 50 mg of THC. In some embodiments, the capsule, caplet, tablet, or edible includes 1 mg to 5 mg, from 5 mg to 10 mg, from 10 mg to 20 mg, from 20 mg to 30 mg, from 30 mg to 40 mg, from 40 mg to 50 mg, from 50 mg to 60 mg, from 60 mg to 70 mg, from 70 mg to 80 mg, from 80 mg to 90 mg, from 90 mg to 100 mg, from 100 mg to 110 mg, from 110 mg to 120 mg, from 120 mg to 130 mg, from 130 mg to 140 mg, from 140 mg to 150 mg, from 150 mg to 200 mg, from 200 mg to 250 mg, from 250 mg to 300 mg, from 300 mg to 350 mg, from 350 mg to 500 mg, from 500 mg to 1,000 mg, or 1,000 mg or above of THC.

In some embodiments, the oral administration includes a liquid. In some embodiments, the liquid includes THC at a dose of 0.001 mg/kg to 0.01 mg/kg, 0.01 mg/kg to 0.1 mg/kg, 0.1 mg/kg to 1 mg/kg, 1 mg/kg to 2 mg/kg, 2 mg/kg to 3 mg/kg, 3 mg/kg to 4 mg/kg, 4 mg/kg to 5 mg/kg, 5 mg/kg to 6 mg/kg, 6 mg/kg to 7 mg/kg, 7 mg/kg to 8 mg/kg, 8 mg/kg to 9 mg/kg, 9 mg/kg to 10 mg/kg, 10 mg/kg to 11 mg/kg, 11 mg/kg to 12 mg/kg, 12 mg/kg to 13 mg/kg, 13 mg/kg to 14 mg/kg, 14 mg/kg to 15 mg/kg, 15 mg/kg to 20 mg/kg, 20 mg/kg to 25 mg/kg, 25 mg/kg to 30 mg/kg, 30 mg/kg to 35 mg/kg, 35 mg/kg to 40 mg/kg, 40 mg/kg to 45 mg/kg, or more than 45 mg/kg, based on the human's weight. In some embodiments, the liquid includes 2.5 mg THC, 5 mg THC, 10 mg THC, 15 mg THC, 25 mg THC, 30 mg THC, from about 25 mg THC to about 35 mg THC, or from about 35 mg THC to about 50 mg of THC. In some embodiments, the liquid includes 1 mg to 5 mg, from 5 mg to 10 mg, from 10 mg to 20 mg, from 20 mg to 30 mg, from 30 mg to 40 mg, from 40 mg to 50 mg, from 50 mg to 60 mg, from 60 mg to 70 mg, from 70 mg to 80 mg, from 80 mg to 90 mg, from 90 mg to 100 mg, from 100 mg to 110 mg, from 110 mg to 120 mg, from 120 mg to 130 mg, from 130 mg to 140 mg, from 140 mg to 150 mg, from 150 mg to 200 mg, from 200 mg to 250 mg, from 250 mg to 300 mg, from 300 mg to 350 mg, from 350 mg to 500 mg, from 500 mg to 1,000 mg, or 1,000 mg or above of THC.

In some embodiments, the treatment method includes an administration of cannabidiol (CBD), caffeine, a selective serotonin reuptake inhibitor (S SRI), or a combination thereof. In some embodiments, the administering is one time per day, two times per day, three times per day, four times per day, five times per day, or six or more times per day. In some embodiments, the human is 3-17 years old, or 18 years old or above. In some embodiments, in addition to treating ASD, one or more comorbid symptoms, disorders, or conditions is also treated. In some embodiments, the one or more comorbid symptoms can be anxiety, depression, obsessive-compulsive disorder (OCD), substance abuse, or a combination thereof.

In one aspect, some embodiments relate to the use of tetrahydrocannabinol (THC) in the manufacture of a medicament for the treatment of autism spectrum disorder (ASD) in a patient. In some embodiments, the patient is 3-17 years old, or 18 years old or above. In some embodiments, the ASD is treated.

In another aspect, some embodiments relate to a composition including a therapeutically effective amount of tetrahydrocannabinol (THC) for use in the treatment of autism spectrum disorder (ASD).

In another aspect, some embodiments relate to the use of tetrahydrocannabinol (THC) in the manufacture of a medicament for the treatment of Attention-Deficit/Hyperactivity Disorder (ADHD) in a patient. In some embodiments, the patient is 3-17 years old, or 18 years old or above. In some embodiments, the ADHD is treated.

In yet another aspect, some embodiments relate to a composition comprising a therapeutically effective amount of tetrahydrocannabinol (THC) for use in the treatment of Attention-Deficit/Hyperactivity Disorder (ADHD).

All publications and patent applications mentioned in this specification are herein incorporated by reference to the same extent as if each individual publication or patent application was specifically and individually indicated to be incorporated by reference.

No admission is made that any reference cited herein constitutes prior art. The discussion of the references states what their authors assert, and the applicants reserve the right to challenge the accuracy and pertinence of the cited documents. It will be clearly understood that, although a number of information sources, including scientific journal articles, patent documents, and textbooks, are referred to herein, this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

EXAMPLES

The following examples are intended to provide illustrations of the application of the present disclosure. The following examples are not intended to completely define or otherwise limit the scope of the disclosure. One of skill in the art will appreciate that many other methods known in the art may be substituted in lieu of the ones specifically described or referenced herein.

Example 1

Failure of Treatment with Zoloft

Patient 1 sought treatment from a psychologist and a psychiatrist for high anxiety, mild depression, and symptoms consistent with obsessive-compulsive disorder (OCD) and ADHD. Symptoms included mild hyperactivity and inattention, pacing, rapid sense of internal time, and deficits in maintaining interpersonal relationships. Patient 1 was also a regular user of alcohol and a recreational user of cocaine. Patient 1 was prescribed selective serotonin reuptake inhibitor (SSRI) Zoloft, at 25 mg with doses increasing up to 200 mg over the course of approximately 6-8 months. The dose of Zoloft/sertraline used was 25-200 mg.

The SSRI was initially effective at treating anxiety, depression, OCD, substance abuse and ADHD at the initial dose and each incremental increase in dose; however, effects wore off at varying intervals after dosage increases.

Example 2

Treatment with THC

Following cessation of efficacy of Zoloft, Patient 1 obtained a prescription for medical marijuana. Patient 1 began by vaporizing marijuana buds and later vaporizing THC wax and oil concentrates. While vaporizing provided some symptom relief, Patient 1 continued to experience all symptoms at varying degrees of severity and continued the regular use of alcohol and the recreational use of cocaine.

Patient 1 began consuming THC in edible form at doses ranging from 10-35 mg every 4-6 hours. Initially, Patient 1 consumed 10-20 mg for approximately 1-2 months, and then increased the dose to 30-35 mg. After consuming THC, Patient 1 reported a slowed perception of time, and after adjusting to the slowed perception of time, a significant reduction in anxiety, depression, and an elimination of OCD and in ADHD-related symptoms which was accompanied by an increased ability to focus and concentrate on reading, writing, and interpersonal interactions. No significant side effects were reported after an initial adjustment period of approximately 2 weeks. Patient 1 used orally consumed THC as a medicament for at least 9 months during which time he observed and recorded the changes in his mood, movements, cognition and behavior while practicing law working, raising children, and otherwise functioning in his daily life. As of the date of this filing, Patient 1 continues to report a significant reduction in anxiety and depression and an elimination of obsessive-compulsive tendencies and elimination of ADHD-related symptoms, with an accompanying increase in focus and attention. Patient 1 continued to use the SSRI Zoloft during approximately the first 2 months of this 9-month period, but thereafter discontinued the use of Zoloft.

Under the influence of orally-consumed THC, Patient 1 reported a reduction in sensitivity to peripheral noise (a reduction in hyperactivity to sensory input) and other distractions, and an increased ability to focus on work, especially reading and writing (a reduction in inattention).

Patient 1 also noticed an increase in his ability to read body language and facial expressions (an improvement in non-verbal communicative behaviors used for social interactions), improvement in interpersonal relationships at home and in the workplace (improvement in developing, maintaining, and understanding relationships), a sense of ease, focus and a reduced propensity to interrupt while orally communicating with others (a reduction in hyperactivity, inattention and impulsivity and an improvement of an oral communication deficit). Patient 1 also reported improvements in coordination and balance, including improvements in fine motor skills (such as handwriting) and resolution of an issue associated with a propensity to drag his left foot while walking. Under the influence of orally-consumed THC, Patient 1 rarely consumed alcohol and stopped using cocaine. Patient 1 also reported an increased ability to visualize images described in writings and an improved sense of direction Patient 1 reports that symptom relief seems tied to THC's slowing of his perception of time, which results in cascading (positive) effects on his mood, movements, cognition and behavior.

Example 3

Group Study

In patients experiencing ADHD-related symptoms or ASD-related symptoms, obtain baseline measures (using, reports, observations or tests described above) of the symptoms and deficits commonly associated with the conditions. Administer THC, or a synthetic substitute such as Marinol® at a specific dose, to half of the group and administer a placebo to the remainder of the participants. The group that is administered THC should be allowed at least 2-3 weeks to acclimate to THC. After the several week adjustment period, all patients should be re-evaluated using the same or similar tests, observations and reports upon which initial measures of symptoms and deficits were made. Consumption of THC should reduce or eliminate symptoms and deficits associated with ASD and ADHD, including without limitation the following: 1) deficits in hyperactivity, impulsivity and inattention (including cognitive and behavioral impairments resulting therefrom); 2) timing deficits; 3) deficits in social interaction; 4) deficits in controlling repetitive-behaviors; 5) deficits in oral communication skills; 6) deficits in motor skills; 7) deficits in visual/spatial problem solving; and 8) deficits in sensory processing.

Example 4

Preparation of *Cannabis* Butter Formulation

This Example illustrates a non-limiting example of a procedure for preparation of a cannabis butter formulation which takes the form of a cookie containing an exemplary amount of cannabis infused organic unsalted butter.

In these studies, butter was used as a solvent to extract cannabis oil from various cannabis plant materials including flower tissues and bud tissues. The extraction could be achieved by heating raw cannabis plant material along with butter and allowing the cannabinoids to be dissolved by the lipids in the butter. The heat-extraction time varied from 10-15 minutes to 24 hours, depending on the amount of cannabis plant materials used and the temperature employed. In a typical extraction process, cannabis butter extracts were prepared by simmering cannabis plant materials and butter on low heat at approximately 200° F. (240° F.-250° F.; never above 300° F.) for about 30-40 minutes. The cannabis plant materials were then removed to produce a cannabis infused organic unsalted butter. If the desirable THC:CBD ratio is not available, a few cannabis butter extracts of different THC:CBD ratio could be mixed to attain the desirable level.

Subsequently, the cannabis infused organic unsalted butter prepared as described above was further formulated into the form of a cookie which included one or more of the following ingredients: organic cane sugar, sea salt, fair-trade organic chocolate, organic cocoa liquor, organic cane sugar, organic cocoa butter, organic natural cocoa powder, pasteurized sweet cream, lactic acid, baking soda, baking powder, organic all-purpose flour, and organic vanilla.

Example 5

Preparation of $CO_2$-extract *Cannabis* Oil Formulation

This Example illustrates a non-limiting example of a procedure for preparation of a $CO_2$-extract cannabis oil formulation which takes the form of a lozenge.

For edible formulations that do not include butter such as, for example, certain types of candies or chocolate products, cannabis oil was extracted from cannabis plant tissues by using a $CO_2$ extraction apparatus. The cannabis extract was prepared by a supercritical fluid extraction process with carbon dioxide ($CO_2$) used as a supercritical fluid. $CO_2$ is generally considered to be a safe, non-toxic material that occurs in nature and can be completely removed from a final clean product in which $CO_2$ is used in a processing step, generally without leaving any trace residue. In a typical $CO_2$ extraction process, supercritical $CO_2$ is inserted into a vessel and pumped through a filter. This separates the cannabis plant matter once the pressure is released. Subsequently, the supercritical $CO_2$ evaporates leaving very little trace $CO_2$ dissolved into the cannabinoid. If the desirable THC:CBD ratio is not available, a few $CO_2$-extract cannabis extracts of different THC:CBD ratio could be mixed to attain the desirable level. The resulting $CO_2$-extract cannabis oil was then incorporated into hard candy or lozenge, which included one or more of the following ingredients: organic cane sugar, organic light corn syrup, reverse osmosis water, organic gum acacia, organic flavors and colors made from organic fruit and vegetable extracts, and sea salt.

Example 6

Reduction of Tolerance Effect from Ingestion of Cannabis-based Formulations and/or Antidepressants This Example summarizes experimental results from studies using the cannabis butter formulation prepared as described in Example 4 and the $CO_2$-extract cannabis oil formulation prepared as described in Example 5 in treating a number of tolerance effects developed in a patient who has previous ingested a cannabis-based pharmaceutical formulation which contained THC as an active ingredient.

Patient 1 sought treatment from a psychologist and a psychiatrist for high anxiety, mild depression, and other symptoms including racing thoughts, obsessive compulsive disorder, substance abuse, ADHD-related symptoms such as, for example, inattention, hyperactivity, impulsivity, and deficits maintaining interpersonal relationships. After treatment with a number of pharmaceutical agents comprising either antidepressant selective serotonin reuptake inhibitor (SSRI; e.g. Zoloft) as described in Example 1, or THC-containing medical marijuana as described in Example 2, Patient 1 reported various symptoms similar to those previously documented on account of significant tolerance effects. The symptoms reported by Patient 1 included high anxiety, mild depression, and symptoms consistent with obsessive-compulsive disorder (OCD) and ADHD. Additional symptoms included, but were not limited to, mild hyperactivity and inattention, pacing, rapid sense of internal time, and deficits in maintaining interpersonal relationships, and in reading and expressing non-verbal cues. To mitigate these tolerance effects, Patient 1 was treated with several different treatment regimens, each of which involved orally administering to Patient 1 the cannabis butter formulation prepared as described in Example 4 and the $CO_2$-extract cannabis oil formulation prepared as described in Example 5 in rotation. Each rotation involved administering the cannabis butter formulation in 2, 3, 4, or 5 consecutive dosages every 4-6 hours, followed by administering of the $CO_2$-extract cannabis oil formulation in 2, 3, 4, or 5 consecutive dosages. The amount of THC and CBD in each dosage ranged from 5 mg to 500 mg and from 0.1 mg to 10 mg, respectively.

TABLE 1

| Experiment Protocol | Result |
| --- | --- |
| A single administration of a cannabis infused butter followed by a single administration of a $CO_2$-extracted cannabis oil | Mild improvement in tolerance effects was observed |
| Two consecutive administrations of a cannabis infused butter followed by two consecutive administrations of a $CO_2$-extracted cannabis oil | Significant improvement in tolerance effects was observed. In some instances, the second consecutive dose was found to have amplifying effects. |
| Two consecutive administrations of a cannabis infused butter followed by three consecutive administrations of a $CO_2$-extracted cannabis oil | Significant improvement in tolerance effects was observed. Third consecutive dose did not appear to amplify or reduce effects significantly. |
| Three consecutive administrations of a cannabis infused butter followed by two consecutive administrations of a $CO_2$-extracted cannabis oil | Significant improvement in tolerance effects was observed. Third consecutive dose did not appear to amplify or reduce effects significantly. Patient reported optimal results while using 3 consecutive day time doses of cannabis infused butter formulation followed by 2 consecutive night time doses of $CO_2$-extracted cannabis oil formulation. |
| Three consecutive administrations of a cannabis infused butter followed by three consecutive administrations of a $CO_2$-extracted cannabis oil | Significant improvement in tolerance effects was observed. Third consecutive dose did not appear to amplify or reduce effects significantly. |
| Four consecutive administrations of a cannabis infused butter followed by four consecutive administrations of a $CO_2$-extracted cannabis oil | At fourth and fifth consecutive dose, patient often noticed tolerance effects. |
| Five consecutive administrations of a cannabis infused butter followed by five consecutive administrations of a $CO_2$-extracted cannabis oil | At fourth and fifth consecutive dose, patient often noticed tolerance effects. |
| Long-term consecutive use of cannabis infused butter | Patient noticed significant tolerance effects after weeks of regular use. |
| Long-term consecutive use of $CO_2$ extracted cannabis oil | Patient noticed significant tolerance effects after weeks of regular use. |
| 5-week consecutive use of THC concentrate in pill form with no food additive | Ineffective. No significant improvement in tolerance effects was observed. |

As shown in TABLE 1, Patient 1 reported that by rotating the two different cannabis-based formulations described above (e.g., one formulation incorporating a cannabis infused butter and another formulation incorporating a $CO_2$-extracted cannabis oil), the symptoms associated with tolerance effect were significantly reduced. In particular, treatment regimens involving rotation of 2 or 3 consecutive doses of cannabis butter formulation followed by 2 or 3 consecutive doses of the $CO_2$-extract cannabis oil formulation, 20-40 mg per dose, drastically reduced the symptoms associated with tolerance effects. In one particular experiment, a treatment regimen involving rotation of 3 consecutive doses of cannabis butter formulation followed by 2 consecutive doses of the $CO_2$-extract cannabis oil formulation, drastically reduced the symptoms associated with tolerance effects to the point of effectively eliminating the very significant tolerance effects that Patient 1 had previously experienced prior to the treatment.

As mentioned above, each reference and publication is hereby incorporated by reference in its entirety.

While certain embodiments have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of treating a human suffering from autism spectrum disorder consisting essentially of administering isolated tetrahydrocannabinol butter to said human in need thereof to effectively treat the autism spectrum disorder is said human in need thereof.

* * * * *